US009089719B2

(12) United States Patent
Simon et al.

(10) Patent No.: US 9,089,719 B2
(45) Date of Patent: *Jul. 28, 2015

(54) NON-INVASIVE METHODS AND DEVICES FOR INDUCING EUPHORIA IN A PATIENT AND THEIR THERAPEUTIC APPLICATION

(75) Inventors: Bruce J. Simon, Mountain Lakes, NJ (US); Joseph P. Errico, Warren, NJ (US); John T. Raffle, Austin, TX (US)

(73) Assignee: Electrocore, LLC, Basking Ridge, NJ (US)

( * ) Notice: Subject to any disclaimer, the term of this patent is extended or adjusted under 35 U.S.C. 154(b) by 654 days.

This patent is subject to a terminal disclaimer.

(21) Appl. No.: 13/024,727

(22) Filed: Feb. 10, 2011

(65) Prior Publication Data

US 2011/0190569 A1 Aug. 4, 2011

Related U.S. Application Data

(63) Continuation-in-part of application No. 13/005,005, filed on Jan. 12, 2011, now Pat. No. 8,868,177, which is a continuation-in-part of application No. 12/964,050, filed on Dec. 9, 2010, which is a (Continued)

(51) Int. Cl.
*A61N 1/40* (2006.01)
*A61N 1/18* (2006.01)
*A61M 21/00* (2006.01)
*A61N 1/36* (2006.01)

(52) U.S. Cl.
CPC .. *A61N 1/40* (2013.01); *A61N 1/18* (2013.01); *A61M 2021/0055* (2013.01); *A61N 1/36017* (2013.01); *A61N 1/36114* (2013.01)

(58) Field of Classification Search
CPC ... A61N 1/18; A61N 1/36014; A61N 1/0456; A61N 1/40; A61N 2/006; A61N 2/008
USPC .................. 607/2, 45–46, 72, 75, 103; 600/9, 600/13–15
See application file for complete search history.

(56) References Cited

U.S. PATENT DOCUMENTS 4,196,737 A 4/1980 Bevilacqua
4,537,195 A * 8/1985 McDonnell .................... 607/46

(Continued)

OTHER PUBLICATIONS

International Search Report and Written Opinion of the International Searching Authority dated Dec. 3, 2011, PCT application PCT/US11/47509, International Filing Date Aug. 12, 2011.

(Continued)

*Primary Examiner* — Catherine Voorhees
(74) *Attorney, Agent, or Firm* — Dentons US LLP

(57) ABSTRACT

A novel non-invasive magnetic stimulator is used to modulate electrical activity of a patient's vagus nerve. Parameters of the stimulation are selected in such a way as to induce a state of euphoria in the patient. The methods and devices may be used for anesthesia, or to treat insomnia, depression, or premenstrual syndromes. They may be used as substitution withdrawal tools for individuals who otherwise would depend on substances and behaviors to achieve a euphoric state of mind, particularly individuals who abusively consume drugs, alcohol or food, or who exhibit behavioral disorders such as compulsive gambling. The devices and methods may also be used to prevent, manage, or relieve stress.

27 Claims, 7 Drawing Sheets

Related U.S. Application Data continuation-in-part of application No. 12/859,568, filed on Aug. 19, 2010, which is a continuation-in-part of application No. 12/408,131, filed on Mar. 20, 2009, now Pat. No. 8,812,112, and a continuation-in-part of application No. 12/612,177, filed on Nov. 4, 2009, now Pat. No. 8,041,428.

(60) Provisional application No. 61/415,469, filed on Nov. 19, 2010.

(56) References Cited

U.S. PATENT DOCUMENTS

| | | | | |
|---|---|---|---|---|
| 5,983,131 | A | 11/1999 | Weaver et al. | |
| 6,770,022 | B2 * | 8/2004 | Mechlenburg et al. | 600/9 |
| 7,658,704 | B2 * | 2/2010 | Fox et al. | 600/13 |
| 8,676,330 | B2 * | 3/2014 | Simon et al. | 607/46 |
| 8,868,177 | B2 * | 10/2014 | Simon et al. | 607/2 |
| 2005/0154426 | A1 * | 7/2005 | Boveja et al. | 607/45 |
| 2005/0261542 | A1 | 11/2005 | Riehl | |
| 2006/0074284 | A1 | 4/2006 | Juola et al. | |
| 2007/0123952 | A1 | 5/2007 | Strother et al. | |
| 2007/0150024 | A1 | 6/2007 | Leyde et al. | |
| 2007/0276449 | A1 | 11/2007 | Gunter et al. | |
| 2008/0051852 | A1 * | 2/2008 | Dietrich et al. | 607/45 |
| 2008/0071329 | A1 | 3/2008 | Giuntoli et al. | |
| 2008/0306325 | A1 | 12/2008 | Burnett et al. | |
| 2009/0157149 | A1 * | 6/2009 | Wahlgren et al. | 607/66 |
| 2009/0204015 | A1 * | 8/2009 | Phillips et al. | 600/544 |
| 2009/0281593 | A9 | 11/2009 | Errico et al. | |
| 2010/0004716 | A1 | 1/2010 | Zimmerling et al. | |
| 2010/0152522 | A1 * | 6/2010 | Roth et al. | 600/13 |
| 2011/0046432 | A1 | 2/2011 | Simon et al. | |
| 2011/0152967 | A1 * | 6/2011 | Simon et al. | 607/45 |
| 2011/0230701 | A1 * | 9/2011 | Simon et al. | 600/9 |
| 2013/0303828 | A1 * | 11/2013 | Hargrove | 600/13 |

OTHER PUBLICATIONS

International Search Report and Written Opinion of the International Searching Authority dated Dec. 22, 2011, PCT application PCT/US11/49844, International Filing Date Aug. 30, 2011.
"Patient's Manual. For Vagus Nerve Stimulation with the VNS Therapy™ System. Mar. 2004". Publication REF 26/0005-6000/1. Cyberonics, Inc., Houston, Texas (Table 1 and pp. 16-21).
Abosch et al. Biological basis for the surgical treatment of depression. Neurosurg Focus 25(1, 2008):E2 (pp. 1-12,DOI: 10.3171/FOC/2008/25/7/E2).
Albert, et al. Deep brain stimulation, vagal nerve stimulation and transcranial stimulation: An overview of stimulation parameters and neurotransmitter release. Neuroscience and Biobehavioral Reviews 33 (2009) 1042-1060.
Al-Mutawaly, et al. The Effects of Pulse Configuration on Magnetic Stimulation. Journal of Clinical Neurophysiology 20(5):361-370, 2003.
Anderson, et al. Decreasing Procedural Pain Over Time of Left Prefrontal rTMS forDepression: Initial Results from the Open-Label Phase of a Multisite Trial (OPT-TMS). Brain Stimul. Apr. 1, 2009; 2(2): 88-92.
Anonymous. Vagus Nerve Stimulation for Treatment-Resistant Depression. TEC Assessment Program 21 (7, 2006).
Arul-Anandam et al. Induction of Hypomanic Episode With Transcranial Direct Current Stimulation. Journal of ECT 26(1,2010): 68-69.
Aziz et al. Magnetic Stimulation of Efferent Neural Pathways to the Human Oesophagus. Gut 33: S53-S70 (Poster Session F218) (1992).
Aziz, Q. et al. Esophageal myoelectric responses to magnetic stimulation of the human cortex and the extracranial vagus nerve. Am. J. Physiol. 267 (Gastrointest. Liver Physiol. 30): G827-G835, 1994.
Basham, et al. Magnetic Stimulation of Neural Tissue: Techniques and System Design. pp. 293-352, In: Implantable Neural Prostheses 1, Devices and Applications, D. Zhou and E. Greenbaum, eds., New York: Springer (2009).

Berridge et al. Affective neuroscience of pleasure: reward in humans and animals. Psychopharmacology (2008) 199:457-480.
Blood et al. Intensely pleasurable responses to music correlate with activity in brain regions implicated in reward and emotion. PNAS 98 (20,2001): 11818-11823.
Bodkin et al. Buprenorphine treatment of refractory depression. Journal of Clinical Psychopharmacology 15(1, 1995): 49-57.
Boecker, et al.The Runner's High: Opioidergic Mechanisms in the Human Brain. Cerebral Cortex 18(2008): 2523-2531.
Borckardt, et al. Reducing Pain and Unpleasantness During Repetitive Transcranial Magnetic Stimulation. Journal of ECT 2006; 22:259-264.
Bejjani et al. Transient acute depression induced by high-frequency deep-brain stimulation. The New England Journal of Medicine 340(19, 1999) 1476-1480.
Bowtell et al. Analytic Calculations of the E-Fields Induced by Time-Varying Magnetic Fields Generated by Cylindrical Gradient Coils. Magnetic Resonance in Medicine 44:782-790 (2000).
Burgdorf et al. The neurobiology of positive emotions. Neuroscience and Biobehavioral Reviews 30 (2006): 173-187.
Carbunaru et al. Toroidal coil models for transcutaneous magnetic stimulation of nerves. IEEE Transactions on Biomedical Engineering. 48 (No. 4, Apr. 2001): 434-441.
Castle et al. Autonomic brainstem nuclei are linked to the hippocampus. Neuroscience 134 (2005) 657-669.
Chae et al. A review of functional neuroimaging studies of vagus nerve stimulation (VNS). Journal of Psychiatric Research 37 (2003) 443-455.
Clarke et al. Early carbon monoxide intoxication: happy to be poisoned? Emerg Med J 2005 ;22:754-755.
Coenen et al. Medial forebrain bundle stimulation as a pathophysiological mechanism for hypomania in subthalamic nucleus deep brain stimulation for Parkinson's disease. Neurosurgery. Jun. 2009;64(6):1106-14.
Dalgleish. The emotional brain. Nat Rev Neurosci. 5(7,2004):583-589.
Davey. Magnetic Stimulation Coil and Circuit Design. IEEE Transactions on Biomedical Engineering, vol. 47 (No. 11, Nov. 2000): 1493-1499.
Ekman et al. The Duchenne smile: Emotional expression and brain physiology II. Journal of Personality and Social Psychology. 1990;58:342-353.
Delitto et al. A Study of Discomfort with Electrical Stimulation. Phys. Ther. 1992; 72:410-424.
Drevets et al. Amphetamine-induced dopamine release in human ventralstriatum correlates with euphoria. Biol Psychiatry 49(2,2001):81-96.
Endicott. PMDD criteria. Diagnostic and Statistical Manual of Mental Disorders, American Psychiatric Association, 2000.
Engineer et al. Reversing pathological neural activity using targeted plasticity. Nature (2011): published online doi:10.1038/nature09656.].
Angstj. The emerging epidemiology of hypomania and bipolar II disorder. Journal of Affective Disorders 50 (1998) 143-151.
Esselle et al. Neural stimulation with magnetic fields: Analysis of induced electric fields, IEEE T11111rans. Biomed. Eng., 39 (Jul. 1992), pp. 693-700.
Faierstein et al. Coil Designs for Localized and Efficient Magnetic Stimulation of the Nervous System. Ph.D. Dissertation, Department of Biomedical Engineering, Case Western Reserve, May 1999. (UMI Microform No. 9940153, UMI Company, Ann Arbor MI).
Faierstein. Coil Designs for Localized and Efficient Magnetic Stimulation of the Nervous System. Ph.D. Dissertation, Department of Biomedical Engineering, Case Western Reserve, May 1999, p. 117 (UMI Microform No. 9940153, UMI Company, Ann Arbor MI).
Feynman et al. The Feynman Lectures on Physics. Volume II. Addison-Wesley Publ. Co. (Reading MA, 1964), p. 15-15.
Fibiger et al. Reward, motivation, cognition: psychobiology of esotelencephalic dopamine systems. In: Mountcastle VB, Bloom FE, Geyer SR, eds. Handbook of physiology: the nervous system IV. Bethesda, MD: American Physiological Society, 1986:647-675.
Finger S. A happy state of mind. Archives of Neurology 1998; 55:241-250.

(56) References Cited

OTHER PUBLICATIONS

Fishman et al. Construct Validity and Frequency of Euphoria Sclerotica in Multiple Sclerosis. The Journal of Neuropsychiatry and Clinical Neurosciences 16 (2004): 350-356.
Follesa P et al. Vagus nerve stimulation increases norepinephrine concentration and the gene expression of BDNF and bFGF in the rat brain. Brain Research 1179(2007): 28-34.
Fried et al. Electric current stimulates laughter. Nature 391(1998): 650.
Froehlich. Opioid peptides. Alcohol health and research world. 132-136, (1997).
Fuchs. The Production of Pleasure by Stimulation of the Brain: An Alleged Conflict Between Science and Philosophy. Philosophy and Phenomenological Research, 36 (4, 1976): 494-505.
George et al. Mechanisms of action of vagus nerve stimulation (VNS). Clinical Neuroscience Research 4 (2004) 71-79.
George et al. Noninvasive techniques for probing neurocircuitry and treating illness: vagus nerve stimulation (VNS), transcranial magnetic stimulation (TMS) and transcranial direct current stimulation (tDCS). Neuropsychopharmacology Reviews (2010) 35, 301-316.
Grant et al. Multicenter Investigation of the Opioid Antagonist Nalmefene in the Treatment of Pathological Gambling. Am J Psychiatry 163(2006):303-312.
Green et al. Conducting polymer-hydrogels for medical electrode applications. Sci. Technol. Adv. Mater. 11 (2010) 014107 (13pp).
Griffin. Perispinal etanercept: Potential as an Alzheimer therapeutic. Journal of Neuroinflammation 2008, 5:3.
Groves et al. Vagal nerve stimulation: a review of its applications and potential mechanisms that mediate its clinical effects. Neurosci Biobehav Rev (2005) 29:493-500.
Haertzen et al. Addiction Research Center Inventory (ARCI): Measurement of euphoria and other drug effects. In M.A. Bozarth (Ed.), Methods of assessing the reinforcing properties of abused drugs (pp. 489-524). New York: Springer-Verlag, (1987).
Hakkinen et al. Which structures are sensitive to painful transcranial stimulation? Electromyogr. clin. Neurophysiol. 1995, 35:377-383.
Hamdy et al. Long-term reorganization of human motor cortex driven by short-term sensory stimulation. Nature Neuroscience 1 (issue 1, May 1998):64-68.
Hamilton. A Rating Scale for Depression. Journal of Neurology, Neurosurgery, and Psychiatry. 23(1960):56-62.
Heimburg et al. On soliton propagation in biomembranes and nerves. PNAS vol. 102 (No. 28, Jul. 12, 2005): 9790-9795.
Hennenlotter et al. The Link between Facial Feedback and Neural Activity within Central Circuitries of Emotion—New Insights from Botulinum Toxin—Induced Denervation of Frown Muscles. Cerebral Cortex 19(2009):537-542.
Henry. Therapeutic mechanisms of vagus nerve stimulation. Neurology 59(6,2002): S3-S14.
Holstege et al. Brain Activation during Human Male Ejaculation. The Journal of Neuroscience 23(27,2003):9185-9193.
Horgan. The forgotten era of brain chips. Scientific American 293(4,2005):66-73.
House, et al. Mood disorders after stroke and their relation to lesion location. A CT scan study. Brain 113(4, 1990):1113-1129.
Hovey et al. The Guide to Magnetic Stimulation, The Magstim Company Ltd, Spring Gardens, Whitland, Carmarthenshire, SA34 0HR, United Kingdom, 2006.
Hsu et al. Analysis of efficiency of magnetic stimulation. IEEE Trans Biomed Eng. Nov. 2003; 50 (11):1276-85.
Jean A. The nucleus tractus solitarius: neuroanatomic, neurochemical and functional aspects. Arch Int Physiol Biochim Biophys 1991;99(5):A3-A52.
Kennedy et al. Dysregulation of Endogenous Opioid Emotion Regulation Circuitry in Major Depression in Women. Arch Gen Psychiatry. 2006;63:1199-1208.
Khedr et al. Aref Electrophysiological study of vocal-fold mobility disorders using a magnetic stimulator. European Journal of Neurology 2002, 9: 259-267.
Khedr et al. Dysphagia and hemispheric stroke: A transcranial magnetic study. Neurophysiologie Clinique/Clinical Neurophysiology (2008) 38, 235-242).
Kjelsås et al. Antecendent and consequences of binge eating episodes in women with an eating disorder. Eat Weight Disord. 9 (1, 2004):7-15.
Klein et al. A case report of hypomania following vagus nerve stimulation for refractory epilepsy .J Clin Psychiatry. Apr. 2003;64(4):485.
Klemenc-Ketis et al. The effect of carbon dioxide on near-death experiences in out-of-hospital cardiac arrest survivors: a prospective observational study. Critical Care 2010, 14:R56.
Koneru et al. Endogenous Opioids: Their Physiological Role and Receptors. Global Journal of Pharmacology, 3 (3,2009): 149-153.
Koob et al. Neuroscience of Addiction. Neuron, vol. 21 (2008), 467-476.
Koutroumanidis. Euphoric (hedonic) theta hypersynchrony in early childhood. Epileptic Disord 2006; 8 (4): 299-304.
Krack et al. Mirthful Laughter Induced by Subthalamic Nucleus Stimulation. Movement Disorders 16 (5, 2001): 867-875].
Lemerrer et al. Reward Processing by the Opioid System in the Brain. Physiol Rev 89(2009): 1379-1412.
Liboff. Signal shapes in electromagnetic therapies: a primer. pp. 17-37 in: Bioelectromagnetic Medicine (Paul J. Rosch and Marko S. Markov, eds.). New York: Marcel Dekker (2004).
Liu et al. On the Induced Electric Field Gradients in the Human Body for Magnetic Stimulation by Gradient Coils in MRI, IEEE Transactions on Biomedical Engineering 50: (No. 7, Jul. 2003) pp. 804-815.
Ma. Neurobiology of Acupuncture: Toward CAM. eCAM 2004;1(1)41-47.
Man et al. Magnetic stimulation for the measurement of respiratory and skeletal muscle function. Eur Respir J 2004; 24: 846-860.
Manji et al. Enhancing Neuronal Plasticity and Cellular Resilience to Develop Novel, Improved Therapeutics for Difficult-to-Treat Depression. Biol Psychiatry 53 (2003):707-742.
Masand et al. Use of stimulants in the medically ill. Psychiatric Clinics of North America 19(3, 1996): 515-547.
Mason et al. A Double-blind, Placebo-Controlled Study of Oral Nalmefene for Alcohol Dependence. Arch Gen Psychiatry 56(1999):719-724.
McAuliffe et al. A Test of Lindesmith's Theory of Addiction: The Frequency of Euphoria Among Long-Term Addicts. The American Journal of Sociology 79 (4,1974): 795-840. See pp. 800-803.
Mega et al. The limbic system: an anatomic, phylogenetic, and clinical perspective. Journal of Neuropsychiatry and Clinical Neurosciences 9 (1997):315-330.
Melville. Bolus Dose of Ketamine Offers Fast-Acting Alleviation of Acute Depression in ED Setting. Medscape Medical News (2010): Article 729622.
Moncrieff et al. Active placebos versus antidepressants for depression. Cochrane Database of Systematic Reviews 2004, Issue 1. Art. No. CD003012.
Montgomery et al. A new depression scale designed to be sensitive to change. Br J Psychiatry 134(1979):382-389.
Nemeroff et al. VNS Therapy in Treatment-Resistant Depression: Clinical Evidence and Putative Neurobiological Mechanisms. Neuropsychopharmacology (2006) 31, 1345-1355.
Nestler et al. Neurobiology of Depression. Neuron 34(2002), 13-25.
Nicoll et al. The Brain's Own Marijuana. Sci Am. 291(6,2004):68-75.
Nilsson et al. Determining the site of stimulation during magnetic stimulation of the peripheral nerve, Electroencephalographs and clinical neurophysiology. vol. 85, pp. 253-264, 1992.
Nutt et al. Development of a rational scale to assess the harm of drugs of potential misuse. Lancet 369 (2007): 1047-1053.
Okun et al. What's in a "Smile?" Intra-operative Observations of Contralateral Smiles Induced by Deep Brain Stimulation. Neurocase, 10(4): 271-279, 2004.
Olney et al. A comparison of magnetic and electric stimulation of peripheral nerves. Muscle Nerve 1990:13:957-963.
Pacher et al.The Endocannabinoid System as an Emerging Target of Pharmacotherapy. Pharmacological Reviews Sep. 2006 vol. 58 No. 3 389-462.

(56) References Cited

OTHER PUBLICATIONS

Pecina et al. Hedonic Hot Spots in the Brain. Neuroscientist 12(6,2006):500-511.

Polak T. et al. Far field potentials from brain stem after transcutaneous vagus nerve stimulation: optimization of stimulation and recording parameters. J Neural Transm. Oct. 2009; 116(10):1237-42.

Price et al. Neurocircuitry of Mood Disorders. Neuropsychopharmacology Reviews 35(2010), 192-216.

Rada et al. Opioids in the hypothalamus control dopamine and acetylcholine levels in the nucleus accumbens. Brain Research 1312(2010) 1-9.

Rafferty et al. Magnetic phrenic nerve stimulation to assess diaphragm function in children following liver transplantation. Pediatr Crit Care Med 2001, 2:122-126.

Rainforth et al. Stress Reduction Programs in Patients with Elevated Blood Pressure: A Systematic Review and Meta-analysis. Curr Hypertens Rep. 9(6,2007):520-528].

Rattay. The basic mechanism for the electrical stimulation of the nervous system. Neuroscience vol. 89, No. 2, pp. 335-346, 1999.

Ressler et al. Role of serotonergic and noradrenergic systems in the pathophysiology of depression and anxiety disorders. Depression and Anxiety 12 (Supplement 1, 2000):2-19.

Richardson. Hypomania: A brief review of conceptual and diagnostic issues. The New Zealand Medical Student Journal No. 10 (2009): 25-28.

Saver et al. The neural substrates of religious experience. The Journal of Neuropsychiatry and Clinical Neurosciences 9 (1997):498-510.

Sawicki et al. Mathematical Modelling of Vagus Nerve Stimulation. pp. 92-97 in: Krawczyk, A. Electromagnetic Field, Health and Environment: Proceedings of EHE'07. Amsterdam, IOS Press, 2008.

Sayette. Does drinking reduce stress? Alcohol Research and Health 23 (4,1999):250-255.

Schachter. Vagus nerve stimulation: mood and cognitive effects. Epilepsy & Behavior 5 (2004) S56-S59.

Schlaepfer et al. Site of Opioid Action in the Human Brain: Mu and Kappa Agonists' Subjective and Cerebral Blood Flow Effects. Am J Psychiatry 155(1998):470-473.

Shafik, A. Functional magnetic stimulation of the vagus nerve enhances colonic transit time in healthy volunteers. Tech Coloproctol (1999) 3:123-12.

Shah et al. Selective Serotonin Reuptake Inhibitors for Premenstrual Syndrome and Premenstrual Dysphoric Disorder: A Meta-Analysis. Obstet Gynecol. 111(5,2008): 1175-1182.

Similowski, T. et al. Cervical magnetic stimulation: a new painless method for bilateral phrenic nerve stimulation in conscious humans. J. Appl. Physiol. 67(4): 1311-1318, 1989.

Sims et al. Assessing the clinical utility of the magnetic stimulator for measuring response latencies in the laryngeal muscles. Otolaryngol Head Neck Surg 1996; 114:761-7.

Skolnick et al. Current perspectives on the development of non-biogenic amine-based antidepressants. Pharmacological Research 43(5,2001):411-422.

Starkstein, Sergio E and Robinson, Robert G. Mechanism of Disinhibition After Brain Lesions. The Journal of Nervous & Mental Disease 185(2,1997): 108-114.

Suihko. Modelling the response of scalp sensory receptors to transcranial electrical stimulation. Med. Biol. Eng. Comput., 2002, 40, 395-401.

Terry. Vagus nerve stimulation: a proven therapy for treatment of epilepsy strives to improve efficacy and expand applications. Conf Proc IEEE Eng Med Biol Soc. 2009;2009:4631-4.

Voruganti et al. Brain imaging research on subjective responses to psychotropic drugs. Acta Psychiatr Scand 2005: 111 (Suppl. 427): 22-28].

Walsh et al. VNS and depression: current status and future directions. Expert Rev. Medical Devices 1(1,2004):155-160.

Wang et al. A three-dimensional finite element method for computing magnetically induced currents in tissues. IEEE Transactions on Magnetics. 30 (Nov. 6, 1994): 5015-5023.

White. Dexamphetamine substitution in the treatment of amphetamine abuse: an initial investigation. Addiction 95(2,2000), 229-238.

Wise. Opiate reward: sites and substrates. Neurosci Biobehav Rev. 13(2-3,1989): 129-33.

Zarate et al. A Randomized Trial of an N-methyl-D-aspartate Antagonist in Treatment-Resistant Major Depression. Arch Gen Psychiatry. 2006;63:856-864.

Zeki. The neurobiology of love. FEBS Letters 581 (2007): 2575-2579.

Zobel et al. Changes in regional cerebral blood flow by therapeutic vagus nerve stimulation in depression: An exploratory approach. Psychiatry Research: Neuroimaging 139 (2005) 165-179.

\* cited by examiner

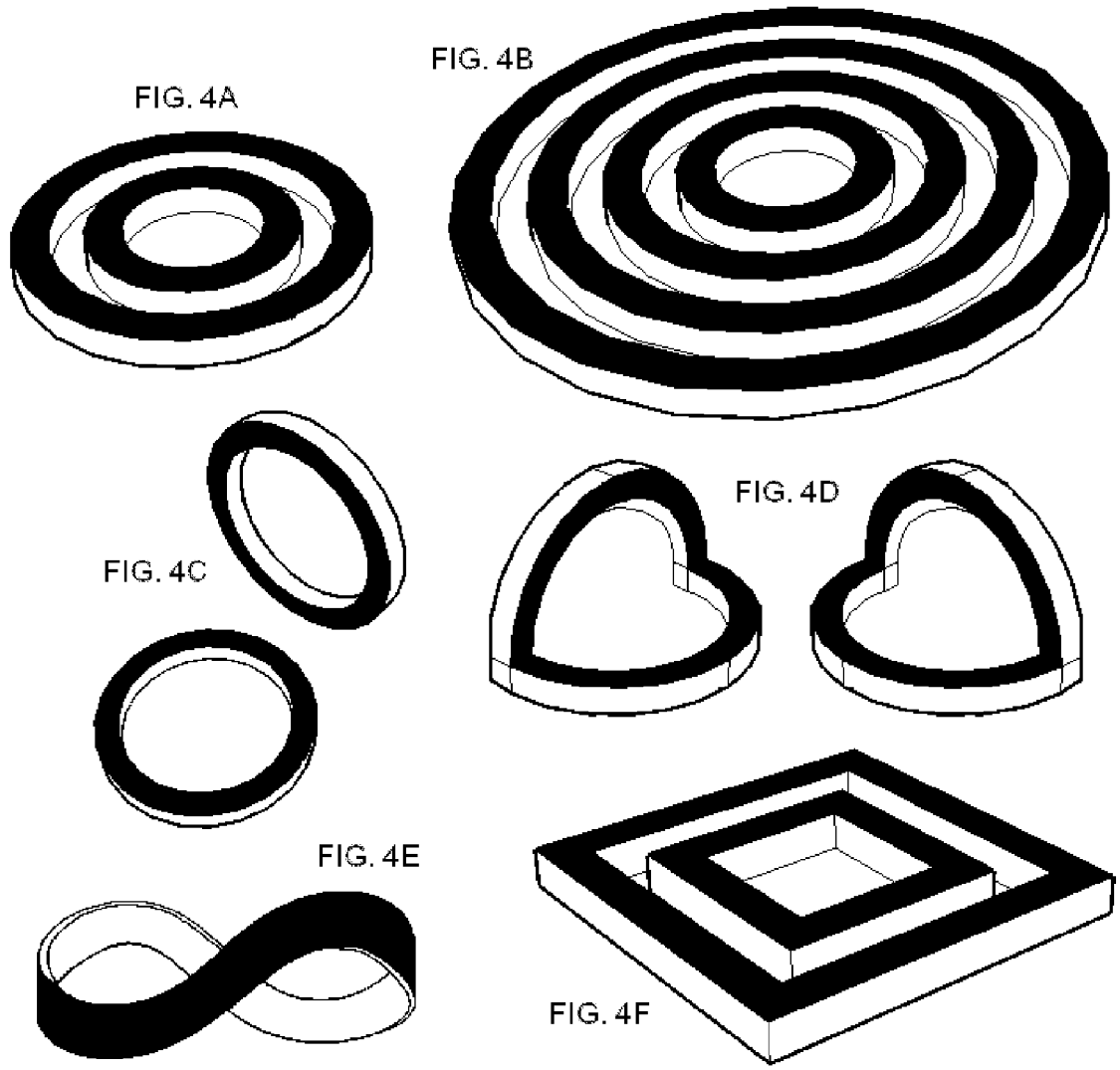

NON-INVASIVE METHODS AND DEVICES FOR INDUCING EUPHORIA IN A PATIENT AND THEIR THERAPEUTIC APPLICATION

CROSS REFERENCE TO RELATED APPLICATIONS

The present application is a Continuation-In-Part of U.S. application Ser. No. 13/005,005 filed Jan. 12, 2011 which published as US2011-0152967 on Jun. 23, 2011; which is a Continuation-In-Part of U.S. application Ser. No. 12/964,050 filed Dec. 19, 2010 which published as US2011-0125203 on May 26, 2011; which claims the benefit of U.S. Provisional Application No. 61/415,469 filed Nov. 19, 2010; each of which is incorporated herein by reference in its entirety. The present application is also a Continuation-In-Part of U.S. application Ser. No. 12/859,568 filed Aug. 9, 2010 which published as US2011-0046432 on Feb. 24, 2011; which is a Continuation-In-Part of U.S. application Ser. No. 12/612,177 filed Nov. 9, 2009 now U.S. Pat. No. 8,041,428 issued on Oct. 18, 2011; which is a Continuation-In-Part of U.S. application Ser. No. 12/408,131 filed Mar. 20, 2009 which published as US2009-0187231 on Jul. 23, 2009; each of which is incorporated herein by reference in its entirety

BACKGROUND OF THE INVENTION

The field of the present invention relates to the delivery of energy impulses (and/or fields) to bodily tissues for therapeutic purposes. It relates more specifically to the use of non-invasive methods and devices, particularly methods that make use of magnetic stimulation devices, to treat depression and/or induce in a patient a euphoric affect or sense of well-being, using energy that is delivered by such devices. The disclosed methods involve stimulation of the vagus nerve to induce euphoria, for example, in individuals needing relief from mental and physical stress, depression, premenstrual syndrome, substance abuse and withdrawal including overeating, and behavioral disorders including compulsive gambling. The disclosed methods and devices may also be used for purposes of anesthesia or as a sleep aid for insomnia.

Treatments for various infirmities sometime require the destruction of otherwise healthy tissue in order to produce a beneficial effect. Malfunctioning tissue is identified and then lesioned or otherwise compromised in order to produce a beneficial outcome, rather than attempting to repair the tissue to its normal functionality. A variety of techniques and mechanisms have been designed to produce focused lesions directly in target nerve tissue, but collateral damage is inevitable.

Other treatments for malfunctioning tissue can be medicinal in nature, but in many cases the patients become dependent upon artificially synthesized chemicals. In many cases, these medicinal approaches have side effects that are either unknown or quite significant. Unfortunately, the beneficial outcomes of surgery and medicines are often realized at the cost of function of other tissues, or risks of side effects.

The use of electrical stimulation for treatment of medical conditions has been well known in the art for nearly two thousand years. It has been recognized that electrical stimulation of the brain and/or the peripheral nervous system and/or direct stimulation of the malfunctioning tissue holds significant promise for the treatment of many ailments, because such stimulation is generally a wholly reversible and non-destructive treatment.

Nerve stimulation is thought to be accomplished directly or indirectly by depolarizing a nerve membrane, causing the discharge of an action potential; or by hyperpolarization of a nerve membrane, preventing the discharge of an action potential. Such stimulation may occur after electrical energy, or also other forms of energy, are transmitted to the vicinity of a nerve [F. RATTAY. The basic mechanism for the electrical stimulation of the nervous system. Neuroscience Vol. 89, No. 2, pp. 335-346, 1999; Thomas HEIMBURG and Andrew D. Jackson. On soliton propagation in biomembranes and nerves. PNAS vol. 102 (no. 28, Jul. 12, 2005): 9790-9795]. Nerve stimulation may be measured directly as an increase, decrease, or modulation of the activity of nerve fibers, or it may be inferred from the physiological effects that follow the transmission of energy to the nerve fibers.

Electrical stimulation of the brain with implanted electrodes has been approved for use in the treatment of various conditions, including movement disorders such as essential tremor and Parkinson's disease. The principle underlying these approaches involves disruption and modulation of hyperactive neuronal circuit transmission at specific sites in the brain. Unlike potentially dangerous lesioning procedures in which aberrant portions of the brain are physically destroyed, electrical stimulation is achieved by implanting electrodes at these sites. The electrodes are used first to sense aberrant electrical signals and then to send electrical pulses to locally disrupt pathological neuronal transmission, driving it back into the normal range of activity. These electrical stimulation procedures, while invasive, are generally conducted with the patient conscious and a participant in the surgery.

Brain stimulation, and deep brain stimulation in particular, is not without some drawbacks. The procedure requires penetrating the skull, and inserting an electrode into brain matter using a catheter-shaped lead, or the like. While monitoring the patient's condition (such as tremor activity, etc.), the position of the electrode is adjusted to achieve significant therapeutic potential. Next, adjustments are made to the electrical stimulus signals, such as frequency, periodicity, voltage, current, etc., again to achieve therapeutic results. The electrode is then permanently implanted, and wires are directed from the electrode to the site of a surgically implanted pacemaker. The pacemaker provides the electrical stimulus signals to the electrode to maintain the therapeutic effect. While the therapeutic results of deep brain stimulation are promising, there are significant complications that arise from the implantation procedure, including stroke induced by damage to surrounding tissues and the neuro-vasculature.

One of the most successful applications of modern understanding of the electrophysiological relationship between muscle and nerves is the cardiac pacemaker. Although origins of the cardiac pacemaker extend back into the 1800's, it was not until 1950 that the first practical, albeit external and bulky, pacemaker was developed. The first truly functional, wearable pacemaker appeared in 1957, and in 1960, the first fully implantable pacemaker was developed.

Around this time, it was also found that electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to DENO, et al., the disclosure of which is incorporated herein by reference).

Another application of electrical stimulation of nerves has been the treatment of radiating pain in the lower extremities by stimulating the sacral nerve roots at the bottom of the spinal cord (see U.S. Pat. No. 6,871,099 to WHITEHURST, et al., the disclosure of which is incorporated herein by reference).

Yet another application of electrical stimulation of nerves has been the treatment of epilepsy and depression by vagus nerve stimulation (VNS) [U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al; U.S. Pat. No. 5,299,569 entitled Treatment of neuropsychiatric disorders by nerve stimulation, to WERNICKE et al]. For these procedures, the left vagus nerve is ordinarily stimulated at a location on the neck by first implanting an electrode there, then connecting the electrode to an electrical stimulator.

Despite the clinical use of VNS in treating epilepsy and depression, a specific mechanism underlying VNS relief of symptoms is not currently known. Vagus afferent fibers innervate several medullary structures, with the nucleus of the tractus solitarius (NTS) receiving bilateral inputs totaling approximately eighty percent of all vagal afferents. The NTS has widespread projections, including direct or multiple synaptic projections to the parabrachial nucleus, vermis, inferior cerebellar hemispheres, raphe nuclei, periaquaductal gray, locus coeruleus, thalamus, hypothalamus, amygdala, nucleus accumbens, anterior insula, infralimbic cortex, and lateral prefrontal cortex, making it difficult to determine the area or neuronal pathway mediating VNS effects. However, functional imaging studies have concluded that VNS may bring about changes in several areas of the brain, including the thalamus, cerebellum, orbitofrontal cortex, limbic system, hypothalamus, and medulla. The stimulation of particular areas of the brain has been suggested as a mechanism for the effects of VNS, but such localized stimulation of the brain may depend upon the parameters of the stimulation (current, frequency, pulse width, duty cycle, etc.). Those parameters may also determine which neurotransmitters are modulated (including norepinephrine, seratonin, and GABA) [Mark S. GEORGE, Ziad Nahas, Daryl E. Bohning, Qiwen Mu, F. Andrew Kozel, Jeffrey Borckhardt, Stewart Denslow. Mechanisms of action of vagus nerve stimulation (VNS). Clinical Neuroscience Research 4 (2004) 71-79; Jeong-Ho Chae, Ziad Nahas, Mikhail Lomarev, Stewart Denslow, Jeffrey P. Lorberbaum, Daryl E. Bohning, Mark S. George. A review of functional neuroimaging studies of vagus nerve stimulation (VNS). Journal of Psychiatric Research 37 (2003) 443-455; G. C. Albert, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009) 1042-1060; GROVES D A, Brown V J. Vagal nerve stimulation: a review of its applications and potential mechanisms that mediate its clinical effects. Neurosci Biobehav Rev (2005) 29:493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4].

To date, the selection of stimulation parameters for VNS has been highly empirical, in which the parameters are varied about some initially successful set of parameters, in an effort to find an improved set of parameters for each patient. A more efficient approach to selecting stimulation parameters might be to select a stimulation waveform that mimics electrical activity in the regions of the brain that one is attempting to stimulate, in an effort to entrain the naturally occurring electrical waveform, as suggested in U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. However, some effects of VNS stimulation, such as effects described herein, are simply discovered by serendipity, then improved upon deliberately.

SUMMARY OF THE INVENTION

Applicants have discovered methods for treating depression and/or inducing euphoria in a patient that are novel, as compared with methods and natural causes that were summarized above. The methods that are disclosed herein are preferably non-invasive, and they comprise stimulating selected nerve fibers, such as those in the vagus nerve, with particular stimulation parameters, preferably using the nerve stimulator devices that are also described herein. The disclosed methods and devices may also be used for purposes of anesthesia or as a sleep aid for insomnia. They may also be useful therapeutically as a controlled substitute and withdrawal tool for individuals who otherwise would depend on unsafe substances and behaviors to achieve an elevated state of mind, particularly individuals who abusively consume food, alcohol, tobacco or drugs, or who exhibit behavioral addictions such as gambling. The methods and devices may also be useful to prevent, manage, or relieve mental or physical stress, depression and/or premenstrual syndromes, thereby reducing the likelihood or severity of consequent health problems such as hypertension, strokes, heart attacks, diabetes, ulcers, and neck or low back pain.

In one aspect of the invention, methods and devices are described to induce a euphoric affect in a patient by utilizing an energy source that transmits energy non-invasively to nervous tissue. In particular, the disclosed devices can transmit energy to, or in close proximity to, a vagus nerve of the patient, in order to temporarily stimulate, block and/or modulate electrophysiological signals in that nerve.

In one of the preferred embodiments, a magnetic stimulator is used to modulate electrical activity of the vagus nerve. The stimulator comprises a source of electrical power, a magnetically permeable toroidal core, and a coil that is wound around the core. The device also comprises a continuous electrically conducting medium in which the coil and core are in contact, wherein the conducting medium has a shape that conforms to the contour of a target body surface of a patient when the medium is applied to the target body surface. For the present medical applications, the device is ordinarily applied to the patient's neck. The source of power supplies a pulse of electric charge to the coil, such that the coil induces an electric current and/or an electric field within the patient. The stimulator is configured to induce a peak pulse voltage sufficient to produce an electric field in the vicinity of a nerve such as the vagus, to cause the nerve to depolarize and reach a threshold for action potential propagation. By way of example, the threshold electric field for stimulation of nerve terminals may be about 8 V/m at 1000 Hz. For example, the device may induce an electric field within the patient of about 10 to 600 V/m and an electrical field with a gradient of greater than 2 V/m/mm.

The preferred magnetic stimulator comprises two toroidal coils and corresponding cores that lie side-by-side, each containing a high-permeability material, wherein current passing through a coil produces a magnetic field within the core of about 0.1 to 2 Tesla. Current passing through a coil may be about 0.5 to 20 amperes, typically 2 amperes, with voltages across each coil of 10 to 100 volts. The current is passed through the coils in bursts of pulses. The burst repeats at 1 Hz to 5000 Hz, preferably at 15-50 Hz. The pulses have duration of 20 to 1000 microseconds, preferably 200 microseconds and there may be 1 to 20 pulses per burst. The preferred magnetic stimulator shapes an elongated electric field of effect that can be oriented parallel to a long nerve, such as the vagus nerve.

By selecting a suitable waveform to stimulate the nerve, the magnetic stimulator produces a correspondingly selective physiological response in an individual patient. In general, the induced electrical signal has a frequency between about 1 Hz to 3000 Hz and a pulse duration of between about 10-1000 microseconds. By way of example, at least one induced electrical signal may be of a frequency between about 15 Hz to 35 Hz. By way of example, at least one induced electrical signal may have a pulsed on-time of between about 50 to 1000 microseconds, such as between about 100 to 300 microseconds. The induced electrical signal may have any desired waveform, which may comprise one or more of: a full or partial sinusoid, a square wave, a rectangular wave, and triangle wave.

Teachings of the present invention demonstrate how non-invasive stimulators may be positioned and used against body surfaces, particularly at a location on the patient's neck under which the vagus nerve is situated. Those teachings also describe the induction of a euphoric affect in a patient, as well as methods for using that induced euphoric affect for purposes of anesthesia, or as a sleep aid for insomnia, or for treating individuals needing relief from mental and physical stress, depression, premenstrual syndromes, substance abuse withdrawal and behavioral addictions. However, it should be understood that application of the methods and devices is not limited to the examples that are given.

The novel systems, devices and methods for treating conditions using the disclosed magnetic stimulator or other non-invasive stimulation devices are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 4 illustrates different embodiments of cores according to the present invention, around which magnetic stimulator coil wires may be wound.

DETAILED DESCRIPTION OF THE PREFERRED EMBODIMENTS

Figure 1:
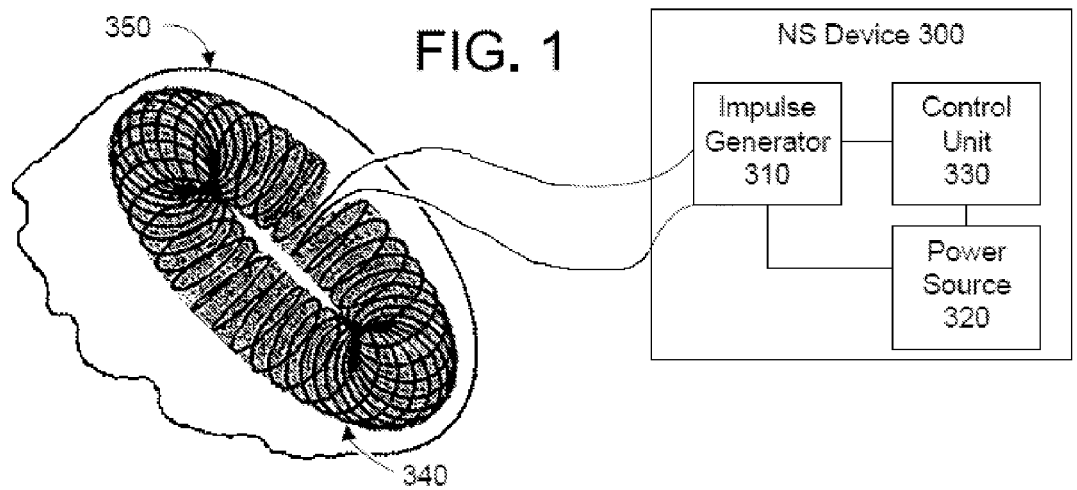
FIG. 1 is a schematic view of a nerve or tissue modulating device according to the present invention, which supplies controlled pulses of electrical current to a magnetic stimulator coil that is continuously in contact with a volume filled with electrically conducting material.

In the present invention, energy is transmitted non-invasively to a patient. The invention is particularly useful for inducing applied electrical impulses that interact with the signals of one or more nerves to achieve a therapeutic result. In particular, the present disclosure describes devices and methods to treat depression and/or induce euphoria in a patient by stimulating the vagus nerve, for example, through non-invasive stimulation at a location on the patient's neck.

In certain preferred embodiments, the present disclosure involves devices and medical procedures that stimulate nerves by transmitting energy to nerves and tissue non-invasively. A medical procedure is defined as being non-invasive when no break in the skin (or other surface of the body, such as a wound bed) is created through use of the method, and when there is no contact with an internal body cavity beyond a body orifice (e.g, beyond the mouth or beyond the external auditory meatus of the ear). Such non-invasive procedures are distinguished from invasive procedures (including minimally invasive procedures) in that invasive procedures do involve inserting a substance or device into or through the skin or into an internal body cavity beyond a body orifice.

Potential advantages of such non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures are sometimes painless or only minimally painful and may be performed without the need for even local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace, and the cost of non-invasive procedures may be reduced relative to comparable invasive procedures.

For example, transcutaneous electrical nerve stimulation (TENS) is non-invasive because it involves attaching electrodes to the surface of the skin (or using a form-fitting conductive garment) without breaking the skin. In contrast, percutaneous electrical stimulation of a nerve is minimally invasive because it involves the introduction of an electrode under the skin, via needle-puncture of the skin. Both TENS and percutaneous electrical stimulation can be to some extent unpleasant or painful, in the experience of patients that undergo such procedures. In the case of TENS, as the depth of penetration of the stimulus under the skin is increased, any pain will generally begin or increase.

The form of non-invasive electrical stimulation with which the present application is primarily concerned is magnetic stimulation. It involves the induction, by a time-varying magnetic field, of electrical fields and current within tissue, in accordance with Faraday's law of induction. Magnetic stimulation is non-invasive because the magnetic field is produced by passing a time-varying current through a coil positioned outside the body, inducing at a distance an electric field and electric current within electrically-conducting bodily tissue. Because the induced electric field and induced current depend not only upon current being passed through wire of the coil, but also upon the permeability of core material around which the coil may be wound, the term coil as used herein refers not only to the current-carrying wire, but also to the core material, unless otherwise indicated. Large, pulsed magnetic fields (PMF) can induce significant electric fields in conducting media, including human tissue. Particular waveforms and amplitudes can stimulate action potentials in nerves, both in vitro and in vivo. Due to the noninvasive nature of the stimulation, PMF devices have found utility in several clinical applications, both therapeutically, e.g., for treating depression via transcranial magnetic stimulation (TMS), and diagnostically, for peripheral nerve stimulation. It is an objective of the present invention to use magnetic stimulation to produce significantly less pain or discomfort, as compared with that experienced by the patient undergoing a treatment with TENS, for a given depth of stimulus penetration. Or conversely, for a given amount of pain or discomfort on the part of the patient (e.g., the threshold at which such discomfort or pain begins), an objective of the present invention is to achieve a greater depth of penetration of the stimulus under the skin.

The principle of operation of magnetic stimulation, along with a description of commercially available equipment and a list of medical applications of magnetic stimulation, is reviewed in: Chris HOVEY and Reza Jalinous, The Guide to Magnetic Stimulation, The Magstim Company Ltd, Spring Gardens, Whitland, Carmarthenshire, SA34 0HR, United Kingdom, 2006. The types of the magnetic stimulator coils that are described there include circular, parabolic, figure-of-eight (butterfly), and custom designs. Additional types of the magnetic stimulator coils are described in U.S. Pat. No. 6,179,770, entitled Coil assemblies for magnetic stimulators, to MOULD; as well as in Kent DAVEY. Magnetic Stimulation Coil and Circuit Design. IEEE Transactions on Biomedical Engineering, Vol. 47 (No. 11, November 2000): 1493-1499 and in HSU K H, Nagarajan S S, Durand D M. Analysis of efficiency of magnetic stimulation. IEEE Trans Biomed Eng. 2003 November; 50 (11):1276-85.

The circuits that are used to send pulses or other waveforms through magnetic stimulator coils are also described by HOVEY and Jalinous in The Guide to Magnetic Stimulation that was cited above. Custom magnetic stimulator circuits for control, impulse generator and power supply have also been described [Eric BASHAM, Zhi Yang, Natalia Tchemodanov, and Wentai Liu. Magnetic Stimulation of Neural Tissue Techniques and System Design. pp 293-352, In: Implantable Neural Prostheses 1, Devices and Applications, D. Zhou and E. Greenbaum, eds., New York: Springer (2009); U.S. Pat. No. 7,744,523, entitled Drive circuit for magnetic stimulation, to EPSTEIN; U.S. Pat. No. 5,718,662, entitled Apparatus for the magnetic stimulation of cells or tissue, to JANILOUS; U.S. Pat. No. 5,766,124, entitled Magnetic stimulator for neuromuscular tissue, to POLSON].

As described in the above-cited publications, the circuits for magnetic stimulators are generally complex and expensive. They use a high current impulse generator that may produce discharge currents of 5,000 amps or more, which is passed through the stimulator coil, and which thereby produces a magnetic pulse. Typically, a transformer charges a capacitor in the impulse generator, which also contains circuit elements that limit the effect of undesirable electrical transients. Charging of the capacitor is under the control of a control unit, which accepts information such as the capacitor voltage, power and other parameters set by the user, as well as from various safety interlocks within the equipment that ensure proper operation, and the capacitor is then discharged through the coil via an electronic switch (e.g., a controlled rectifier) when the user wishes to apply the stimulus. Greater flexibility is obtained by adding to the impulse generator a bank of capacitors that can be discharged at different times. Thus, higher impulse rates may be achieved by discharging capacitors in the bank sequentially, such that recharging of capacitors is performed while other capacitors in the bank are being discharged. Furthermore, by discharging some capacitors while the discharge of other capacitors is in progress, by discharging the capacitors through resistors having variable resistance, and by controlling the polarity of the discharge, the control unit may synthesize pulse shapes that approximate an arbitrary function.

In the preferred embodiments of the present invention, the disclosed methods use a magnetic stimulation device that requires significantly less electrical current to be passed through its coil(s) than magnetic stimulation devices currently known in the art. That low-current magnetic stimulation device also has control circuits, impulse generators, and power supplies that are significantly less complex than magnetic stimulation devices currently known in the art. In fact, the magnetic stimulation device used in preferred embodiments of the present invention requires so little power that it can be operated using conventional low-voltage batteries, thereby reducing the cost to manufacture the device and allowing for portability of the device. The low-current magnetic stimulation device was disclosed in Applicant's copending U.S. patent application Ser. No. 13/005,005, published as US Pat. Pub. No. 2011/0152967, entitled NON-INVASIVE METHODS AND DEVICES FOR INDUCING EUPHORIA IN A PATIENT AND THEIR THERAPEUTIC APPLICATION, to SIMON et al, which is hereby incorporated by reference in its entirety for all purposes.

A practical disadvantage of conventional magnetic stimulator coils is that they overheat when used over an extended period of time, because large coil currents are required to reach threshold electric fields in the stimulated tissue. At high repetition rates, currents can heat the coils to unacceptable levels in seconds to minutes, depending on the power levels and pulse durations and rates. Accordingly, coil-cooling equipment is used, which adds complexity to the magnetic stimulator coils. Two approaches to overcome heating are to cool the coils with flowing water or air or to increase the magnetic fields using ferrite cores (thus allowing smaller currents). For some applications where relatively long treatment times at high stimulation frequencies may be required, e.g. treating asthma by stimulating the vagus nerve, neither of these two approaches may be adequate. Water-cooled coils overheat in a few minutes. Ferrite core coils heat more slowly due to the lower currents and heat capacity of the ferrite core, but they also cool slowly and do not allow for water-cooling because the ferrite core occupies the volume where the cooling water would flow. One solution to this problem is to use a core that contains ferrofluids [U.S. Pat. No. 7,396,326 and published applications US20080114199, US20080177128, and US20080224808, all entitled Ferrofluid cooling and acoustical noise reduction in magnetic stimulators, respectively to GHIRON et al., RIEHL et al., RIEHL et al. and GHIRON et al.]. However, even the use of ferrofluids may be inadequate when long treatment times at high stimulation frequencies may be required.

In preferred embodiments of the present invention, Applicant's above-mentioned low-current magnetic stimulation device is used, which requires so little electrical current to be passed through its coil(s) that no special cooling apparatus is required to operate the device. That device may therefore be operated at high repetition rates for an indefinite period of time. In other embodiments or the present invention, higher current magnetic stimulation coils are used, which may be cooled using methods and devices that Applicant disclosed in co-pending U.S. patent application Ser. No. 12/859,568, published as US Pat. Pub. No. 2011/0046432, entitled Non-invasive Treatment of Bronchial Constriction, to SIMON, which is hereby incorporated by reference in its entirety for all purposes. That application also disclosed methods and devices for the stimulation of nerves other than magnetic stimulation devices and methods, including mechanical and/or acoustical, optical and/or thermal, and electrode-based electrical methods and devices, each of which may be used in alternate embodiments of the present invention in lieu of, or in addition to, the preferred magnetic stimulation devices and methods.

Another problem that is sometimes encountered during magnetic stimulation is the unpleasantness or pain that is experienced by the patient in the vicinity of the stimulated tissue. Little is known about the mechanism that produces the pain, although it is generally recognized that magnetic stimulation produces less pain than its electrode-based counterpart. Most investigations that address this question examine pain associated with transcranial stimulation.

ANDERSON et al found that when magnetic stimulation is repeated over the course of multiple sessions, the patients adapt to the pain and exhibit progressively less discomfort [Berry S. ANDERSON, Katie Kavanagh, Jeffrey J. Borckardt, Ziad H. Nahas, Samet Kose, Sarah H. Lisanby, William M. McDonald, David Avery, Harold A. Sackeim, and Mark S. George. Decreasing Procedural Pain Over Time of Left Prefrontal rTMS for Depression: Initial Results from the Open-Label Phase of a Multisite Trial (OPT-TMS). Brain Stimul. 2009 April 1; 2(2): 88-92]. Other than waiting for the patient to adapt, strategies to reduce the pain include: use of anesthetics placed on or injected into the skin near the stimulation and placement of foam pads on the skin at the site of stimulation [Jeffrey J. BORCKARDT, Arthur R. Smith, Kelby Hutcheson, Kevin Johnson, Ziad Nahas, Berry Anderson, M. Bret Schneider, Scott T. Reeves, and Mark S. George. Reducing Pain and Unpleasantness During Repetitive Transcranial Magnetic Stimulation. Journal of ECT 2006; 22:259-264], use of nerve blockades [V. HAKKINEN, H. Eskola, A. Yli-Hankala, T. Nurmikko and S. Kolehmainen. Which structures are sensitive to painful transcranial stimulation? Electromyogr. clin. Neurophysiol. 1995, 35:377-383], the use of very short stimulation pulses [V. SUIHKO. Modelling the response of scalp sensory receptors to transcranial electrical stimulation. Med. Biol. Eng. Comput., 2002, 40, 395-401], and providing patients with the amount of information that suits their personalities [Anthony DELITTO, Michael J Strube, Arthur D Shulman, Scott D Minor. A Study of Discomfort with Electrical Stimulation. Phys. Ther. 1992; 72:410-424]. U.S. Pat. No. 7,614,996, entitled Reducing discomfort caused by electrical stimulation, to RIEHL discloses the application of a secondary stimulus to counteract what would otherwise be an uncomfortable primary stimulus.

However, these methods of reducing pain or discomfort on the part of the stimulated patient are not always successful or practical. Accordingly, in the preferred embodiments of the present invention, Applicant's above-mentioned low-current magnetic stimulation device is used, which produces significantly less pain or discomfort (if any) to the patient than magnetic stimulator devices that are currently known in the art.

To achieve the objectives of the present invention, Applicant's above-mentioned low-current magnetic stimulation device uses an efficient method to produce electric fields in tissue noninvasively, namely, to use a toroidal winding around a high magnetic permeability material core, embedded in a conducting medium [Rafael CARBUNARU and Dominique M. Durand. Toroidal coil models for transcutaneous magnetic stimulation of nerves. IEEE Transactions on Biomedical Engineering. 48 (No. 4, April 2001): 434-441]. The conducting medium must have direct contact with skin for current to flow from the coil into the tissue. In essence, Applicant's device produces a transcutaneous current, similar to a transcutaneous electrical nerve stimulation (TENS) device, but with greater depth of penetration and virtually no unpleasant peripheral nerve stimulation. In addition, to generate electric fields equivalent to other PMF devices, toroidal stimulators require only about 0.001-0.1 of the current and produce virtually no heating. It is understood that the magnetic field of a toroidal magnetic stimulator remains essentially within the toroid, and that when referring to this device as a magnetic stimulator, it is in fact the electric fields and/or currents that are induced outside the stimulator that produce an effect in the patient, not the magnetic field.

To the Applicant's knowledge, no significant development of toroidal-coil magnetic stimulators has taken place beyond what was reported in the above-mentioned CARBUNARU and Durand publication and the dissertation upon which it was based [Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999. (UMI Microform Number: 9940153, UMI Company, Ann Arbor Mich.)]. Toroidal coils or partial-toroids were mentioned in the following patents or patent applications, but they did not develop the use of a conducting medium in contact with skin: US20080027513, entitled Systems And Methods For Using A Butterfly Coil To Communicate With Or Transfer Power To An Implantable Medical Device, to CARBUNARU; U.S. Pat. No. 7,361,136, entitled Method and apparatus for generating a therapeutic magnetic field, to PARKER; U.S. Pat. No. 6,527,695, entitled Magnetic stimulation coil and circuit design, to DAVEY et al.; U.S. Pat. No. 6,155,966, entitled Apparatus and method for toning tissue with a focused, coherent electromagnetic field, to PARKER; U.S. Pat. No. 4,915,110, entitled Therapeutic electrostatic device, to KITOV; US20070032827, entitled Methods and apparatus for producing therapeutic and diagnostic stimulation, to KATIMS; US20100222629, entitled Method and apparatus for magnetic induction therapy, to BURNETT et al. The latter application to BURNETT et al. only notes that "in the paper titled 'Contactless Nerve Stimulation and Signal Detection by Inductive Transducer' presented at the 1969 Symposium on Application of Magnetism in Bioengineering, Maass et al. disclosed that a nerve threading the lumen of a toroid could be stimulated by a magnetic field."

The lack of development is apparently due to the difficulty of embedding the coil in a practical conducting medium and having that medium be safely in direct contact with human skin. The only reported toroidal-coil magnetic stimulation device used to stimulate human nerves was described in the above-cited dissertation by Rafael Carbunaru FAIERSTEIN, and it embedded the coil in agar. Agar degrades in time and is not ideal to use against skin, presenting difficulties with cleaning it from a patient and within a device. Furthermore, as disclosed there, the toroid needs to be surrounded by conducting medium above, below and around it, making for a relatively bulky device that is difficult to apply to target tissue having small cross sectional area. Furthermore, the device that FAIERSTEIN discloses cannot be applied to the surface of the skin at an arbitrary orientation.

In certain preferred embodiments of the present invention involving the induction of euphoric affect in a patient, Applicant's low-current, toroidal-coil magnetic stimulation device may be used. The device may be applied to body surfaces having an arbitrary orientation with respect to the long-axis of the component containing the coil. Additional advantages of embodiments of Applicant's device are that the embodiments are compact and portable, and that they may be adapted for use in nerve and tissue stimulation applications that treat diverse medical conditions.

Applicant's co-pending patent application that was mentioned above Ser. No. 13/005,005, published as US Pat. Pub. No. 2011/0152967, entitled NON-INVASIVE METHODS AND DEVICES FOR INDUCING EUPHORIA IN A PATIENT AND THEIR THERAPEUTIC APPLICATION, disclosed methods for using the device to treat such conditions as post-operative ileus, dysfunction associated with TNF-alpha in Alzheimer's disease, postoperative cognitive dysfunction, rheumatoid arthritis, bronchoconstriction, urinary incontinence and/or overactive bladder, and sphincter of Oddi dysfunction.

Another of Applicant's co-pending applications, Ser. No. 13/005,005, published as US Pat. Pub. No. 2011/0152967 entitled Non-invasive Treatment of Neurodegenerative Diseases, disclosed methods and devices for treating neurodegenerative diseases more generally, including Alzheimer's disease and its precursor mild cognitive impairment (MCI), Parkinson's disease (including Parkinson's disease dementia) and multiple sclerosis, as well as postoperative cognitive dysfunction and postoperative delirium.

The treatment that was disclosed for postoperative delirium relied upon stimulation of the amygdala and other structures of the brain that influence emotions (in that case delirium and its associated emotion of fear). A treatment was also disclosed for treating Parkinson's disease, involving simultaneous and synergistic electrical stimulation along with bright light stimulation, which may improve the mood of the patient. The present application discloses additional methods and devices that are intended to modify a patient's state of mind. In particular, Applicant has discovered and discloses herein that vagal nerve stimulation may under certain conditions induce a euphoric state of mind in a patient.

Methods are also disclosed for using the induced euphoria in individuals needing relief from mental and physical stress, depression, premenstrual syndromes, substance abuse and withdrawal including overeating, and behavioral addictions including gambling. Furthermore, it is disclosed herein that the induction of euphoria may be used for purposes of anesthesia or as a sleep aid for insomnia.

The term euphoria is used in multiple related senses, as evidenced by the definitions of the word "euphoria" that are given by different medical dictionaries:

1. a feeling or state of well-being or elation.
2. an exaggerated or abnormal sense of physical and emotional well-being not based on reality or truth, disproportionate to its cause, and inappropriate to the situation, as commonly seen in the manic stage of bipolar disorder, some forms of schizophrenia, organic mental disorders, and toxic and drug-induced states. (Mosby's Medical Dictionary, 8th edition).

Elevated mood. Euphoria is a desirable and natural occurrence when it results from happy or exciting events. An excessive degree of euphoria that is not linked to events is characteristic of hypomania or mania, abnormal mood states associated with bipolar disorders. (MedTerms™ Medical Dictionary).

A feeling of great happiness or well-being. Euphoria may be a side effect of certain drugs. (National Cancer Institute Dictionary of Cancer Terms).

An intense feeling of elation or well-being. Many marijuana users experience temporary euphoria. (Gale Encyclopedia of Medicine, 2008).

A feeling of well-being or elation; especially: one that is groundless, disproportionate to its cause, or inappropriate to one's life situation. (Merriam-Webster's Medical Dictionary and Medline Plus of the U.S. National Library of Medicine)

More nuanced definitions of the word euphoria may be made, by referring to particular populations of euphoric individuals, such as drug users who achieve euphoric states through use of drugs such as cocaine, cannabis, methamphetamines and their derivatives such as MDMA (ecstasy), as well as opioids and morphine derivatives such as heroin. For drug users, different usages of the term may refer to a prolonged "high" euphoric feeling, or alternatively to an acute euphoric feeling of "rush" [William E. McAULIFFE and Robert A. Gordon. A Test of Lindesmith's Theory of Addiction: The Frequency of Euphoria Among Long-Term Addicts. The American Journal of Sociology 79 (4, 1974): 795-840. See pp. 800-803].

Estimation of the degree of euphoria may also be made by a trained observer using a standard scale, such as the following, which was used in experiments in which stimulating electrodes were implanted in various sites of subjects' brains: 1. The patient becomes relaxed, at ease, has a feeling of well-being, and/or may be a little sleepy (Positive I). 2. The patient is definitely changed, is in a good mood, and feels good. He is relaxed, at ease, and enjoying himself. He frequently smiles. There is slight euphoria, but the behavior is within normal limits. He may want more stimulations (Positive II). 3. The euphoria is definitely beyond normal limits. The patient laughs out loud, enjoys himself, positively likes the stimulation and wants more (Positive III). [Alan E. Fuchs. The Production of Pleasure by Stimulation of the Brain: An Alleged Conflict Between Science and Philosophy. Philosophy and Phenomenological Research, 36 (4, 1976): 494-505].

Another method of ascertaining the degree of pleasure that is induced by a particular form of stimulation is the delphi method in which experts, experienced with many forms of pleasurable stimulation, are asked to rank or otherwise quantify the different forms of stimulation [Nutt D, King L A, Saulsbury W, Blakemore C. Development of a rational scale to assess the harm of drugs of potential misuse. Lancet 369 (2007): 1047-1053].

Ascertaining the euphoric individual's emotional state may also be made by the individual himself through the use of questionnaires such as the Addiction Research Center Inventory. The questionnaires may be used to distinguish different states of euphoria that are produced by different drugs, as well as by alcohol consumption [C. A. HAERTZEN and J. E. Hickey (1987). Addiction Research Center Inventory (ARCI): Measurement of euphoria and other drug effects. In M. A. Bozarth (Ed.), Methods of assessing the reinforcing properties of abused drugs (pp. 489-524). New York: Springer-Verlag]. The ARCI answer sheet is in true-false format, wherein the respondent answers many questions such as "I feel as if I would be more popular with people today" and "I feel drowsy". The totality of answers to those questions by an individual may be used to sub-classify drug-induced euphoria according to drug types. Those sub-classifications are presumably a reflection of the different neuronal circuits that are activated or inhibited by different drugs. Such circuits are described below in connection with the neurophysiology of euphoria. Scoring high on the "MBG" scale of the ARCI would be indicative of euphoria. Although it was designed for an evaluation of the effects of different drugs, the ARCI may be used for other forms of stimulation as well. For example, acupuncture has been found to increase MBG scores, although not to the extent that is associated with drugs in the MBG group (morphine, Benzedrine) [Sheng-Xing Ma. Neurobiology of Acupuncture: Toward CAM. eCAM 2004; 1(1) 41-47].

Similarly, a differential classification of euphorias might be attempted with poisons that unintentionally or accidentally produce states of euphoria. Carbon monoxide poisoning appears to be most common among the population at large, and mass euphoria caused by carbon monoxide from defective heating equipment has been reported [S F J Clarke, A Crosby, D Kumar. Early carbon monoxide intoxication: happy to be poisoned? Emerg Med J 2005; 22:754-755].

Occupational exposure to organic solvents and gases may also cause euphoria through their inhalation. These solvents and gases include spray paint, paint thinner, glue, gasoline, varnishes, art or office supply solvents, butane lighters and propane tanks, aerosol propellants and associated solvents, refrigerant gases, aliphatic nitrites such as cyclohexyl nitrite that is sold as a head cleaner for video recorders, and nitrous oxide sold as a whipped-cream propellant. The toluene (methyl-benzene) component of such solvents is a particularly potent poison because it shows a high affinity to myelin, easily producing a euphoric effect by disrupting transmission of myelinated nerves. For this reason, toluene inhalation (glue sniffing) is a common form of substance abuse among children and young adults.

Nitrogen narcosis or "rapture of the deep" is another well-known form of euphoria that affects scuba divers who descend underwater to depths of more than 30 meters. Gases other than nitrogen in the diver's tank will also cause narcosis, to an extent that is determined by lipid solubility of the gas. It is thought that the gasses dissolve into nerve membranes and cause disruption in nerve transmissions. These effects are similar to various concentrations of nitrous oxide (laughing gas) or other gases used for anesthesia, wherein ligand-gated ion channels are modulated, stimulating the mesolimbic reward pathway of the brain by inducing dopamine release.

Children and young adults are also known to induce a temporary state of euphoria through a procedure known as "the choking game" or "the fainting game", involving hyperventilation followed by steps in which blood flow to the brain is restricted by pressing against the carotid artery, or the individuals hold their breath. Hypoxia, hypercarbia, and alkalosis follow, resulting in a brief sense of euphoria. Reflexes involving baroreceptors in the neck may also be involved.

Euphoria may also be produced through physical exercise, particularly in endurance runners who experience "runner's high". The physiological basis for that euphoria appears to involve the release of endogenous opioids (endorphins) from the pituitary gland, although mechanisms involving exercise-enhanced brain aminergic synaptic transmission (noradrenaline, dopamine and serotonin) and body-temperature might also be involved [Henning Boecker, Till Sprenger, Mary E. Spilker, Gjermund Henriksen, Marcus Koppenhoefer, Klaus J. Wagner, Michael Valet, Achim Berthele, and Thomas R. Tolle. The Runner's High: Opioidergic Mechanisms in the Human Brain. Cerebral Cortex 18 (2008): 2523-2531].

Stress may be generated by many forms of activity other than aerobic physical exercise, and as the stress resolves successfully, the person who experiences this so-called eustress may feel euphoric. Such activities include other forms of physical activity such as weight training or sexual activity; winning in competition including gambling or video-games; work-related success such as intellectual problem solving, test-taking or having a grant application funded; and deliberately exciting, suspenseful or dangerous activities such as military conflict, bungee jumping, race-car driving, watching a suspenseful movie, or discovery activities. Other stress-related events may be unintentional, such as near-death experiences that result in joyous or transcendental euphoria. Physiological interpretations of such eustress-induced euphoria involve anoxia, hypercapnia, the presence of endorphins, ketamine, and serotonin, and abnormal activity of the temporal lobe or the limbic system of the brain [Zalika Klemenc-Ketis, Janko Kersnik, Stefek Grmec. The effect of carbon dioxide on near-death experiences in out-of-hospital cardiac arrest survivors: a prospective observational study. Critical Care 2010, 14:R56].

Individuals who suffer from the eating disorder bulimia nervosa reportedly experience euphoria as an antecedent to binge eating. A sense of euphoria may also terminate binge eating in eating disorders other than anorexia nervosa [Kjelsås E, Børsting I, Gudde C B. Antecendent and consequences of binge eating episodes in women with an eating disorder. Eat Weight Disord. 9 (1, 2004):7-15].

A form of euphoria (shivers-down-the-spine) may be experienced by individuals listening to music [Anne J. Blood and Robert J. Zatorre. Intensely pleasurable responses to music correlate with activity in brain regions implicated in reward and emotion. PNAS 98 (20, 2001): 11818-11823].

The euphoria of romantic and maternal love is triggered by sensory inputs, particularly visual inputs and odors. They activate regions of the brain that are specific to each type of euphoria, as well as overlapping regions in the brain's reward system that coincide with areas rich in oxytocin and vasopressin receptors. Both deactivate a common set of brain regions associated with negative emotions, social judgment and the assessment of other people's intentions and emotions [S. Zeki. The neurobiology of love. FEBS Letters 581 (2007): 2575-2579]. The deactivation occurs in regions of the amygdala, which is also deactivated in a cocaine-induced "rush" euphoria.

The most intense reciprocated romantic love is strongly coupled to sexual desire, and the two faculties share common areas in the brain. The euphoria during orgasm includes activation in and around the ventral tegmental area (VTA) of the brain, which is also activated during the "rush" euphoria of cocaine and heroin users [Gert Holstege, Janniko R. Georgiadis, Anne M. J. Paans, Linda C. Meiners, Ferdinand H. C. E. van der Graaf, and A. A. T. Simone Reinders. Brain Activation during Human Male Ejaculation. The Journal of Neuroscience 23(27, 2003):9185-9193].

A small percentage of epileptics experience one of two types of ecstatic seizures. One type is a euphoria or feeling of deep pleasure. The second is a primarily cognitive form of euphoria in which the individual feels the unity, harmony, or joy of reality. Because a significant number of historically important religious or mystical individuals are thought to have been epileptics, it is thought that the neurophyiological substrate of religious or mystical euphoria is related to epilepsy [Jeffrey L. Saver, John Rabin. The neural substrates of religious experience. The Journal of Neuropsychiatry and Clinical Neurosciences 9 (1997):498-510].

A euphoric state of mind is also exhibited in approximately nine percent of multiple sclerosis patients, of the type known as euphoria sclerotica. However, unlike most other forms of euphoria, it is also characterized by such features as uncontrollable laughter, disinhibition, and low agreeableness [Irina FISHMAN, Ralph H. B. Benedict, Rohit Bakshi, Roger Priore, Bianca Weinstock-Guttman. Construct Validity and Frequency of Euphoria Sclerotica in Multiple Sclerosis. The Journal of Neuropsychiatry and Clinical Neurosciences 16 (2004): 350-356; Finger S: A happy state of mind. Archives of Neurology 1998; 55:241-250].

Hypomania is an often euphoric state of mind lasting four or more days that is experienced by individuals with bipolar disease. Hypomania is distinguished from mania by the absence of psychotic symptoms and by the former's lower degree of impact on functioning. Although "Extremely happy mood, over euphoristic" is one of the characteristics of hypomania, an individual may instead have the characteristic of "More irritable, impatient." In that sense, the hypomania resembles individuals who may become either euphoric or irritable during high fever, or who contain toxins that may be due for example to infection or encephalopathy. In any case, the hypomanic individual may ordinarily feel the need for less sleep; be extremely energetic, active and motivated to work; be more outgoing and talkative than usual; think faster, including rapid formulation of puns and jokes with more than usual laughter (Witzelsucht); and take risks, including the adverse risk of taking intoxicating substances. An individual with depression and hypomanic episodes will lead to a diagnosis of bipolar II, but depression with mania leads to a diagnosis of bipolar I disorder.

Hypomania may also be induced as a side effect of drugs. In particular, amphetamines that promote dopamine release and inhibit its reuptake have been shown to either precipitate hypomania in patients with bipolar disease or induce a "hypomanic-like" state in otherwise healthy subjects [Wayne C. Drevets, Clara Gautier, Julie C. Price, David J. Kupfer, Paul E. Kinahan, Anthony A. Grace, Joseph L. Price, and Chester A. Mathis. Amphetamine-induced dopamine release in human ventralstriatum correlates with euphoria. Biol Psychiatry 49(2, 2001):81-96]. If an individual has hypomanic symptoms without accompanying periods of depression or drug side effects, the individual may simply have a hypomania-like temperament or personality (e.g., an enthusiastic and outgoing workaholic, or an ENTJ personality according to the Myers-Briggs classification) [Jules Angst. The emerging epidemiology of hypomania and bipolar II disorder. Journal of Affective Disorders 50 (1998) 143-151; Thomas Hugh Richardson. Hypomania: A brief review of conceptual and diagnostic issues. The New Zealand Medical Student Journal Number 10 (2009): 25-28].

Hypomania is a type of disinhibition syndrome, which may require both a lesion in a specific brain area (such as the orbitofrontal and basotemporal cortices) as well as involvement of the brain's right hemisphere. Thus, brain asymmetries may play an important role in the production of disinhibited behaviors such as hypomania [STARKSTEIN, Sergio E and Robinson, Robert G. Mechanism of Disinhibition After Brain Lesions. The Journal of Nervous & Mental Disease 185(2, 1997): 108-114]. However, apart from the induction of euphoria in hypomania and focal epilepsy, there is little evidence that lesions, such as those produced by head injuries, brain tumors, and stroke, produce euphoria [Allan HOUSE, Martin Dennis, Charles Warlow, Keith Hawton, and Andy Molyneux. Mood disorders after stroke and their relation to lesion location. A CT scan study. Brain 113(4, 1990):1113-1129].

Young children are unable to describe any euphoria that they may experience, so the existence of euphoria in children must therefore ordinarily be inferred from their behavior. However, one type of euphoria can be measured from an electroencephalogram. That euphoric state is unique to the developing brains of children and is known as euphoric theta hypersynchrony. It can be induced by maternal affection [Michael Koutroumanidis. Euphoric (hedonic) theta hypersynchrony in early childhood. Epileptic Disord 2006; 8 (4): 299-304]. In adults, particular brain waves are not associated with euphoria, but an alpha wave may be associated with relaxation. Alpha waves originate from the occipital lobe during wakeful relaxation with closed eyes, and an individual may be trained to produce them through biofeedback and meditation.

Euphoria in animals must also ordinarily be inferred from their behavior, such as facial expressions in mammals, species-specific vocalization, frequency of self-stimulating behavior, or by observing that the animal prefers to place itself in a location (or other environment) where it had been previously stimulated. For example, smiling and laughing are intrinsic behaviors that indicate happiness, and pleasure in rats is indicated by ultrasonic chirps. Such signs of happiness in animals are useful in neurophysiological experiments that are intended to determine the brain locations and pathways that are involved in happiness [Jeffrey BURGDORF and Jaak Panksepp. The neurobiology of positive emotions. Neuroscience and Biobehavioral Reviews 30 (2006): 173-187]. Regions of the brain can also be identified as being associated with emotion such as euphoria by stimulating them electrically (including self-stimulating behavior using permanently implanted electrodes), by placing lesions within regions of the brain, or by identifying within them receptors for chemicals that influence emotional state. Neuroimaging pertaining to the physiology of psychotrophic drugs has also been performed, in an effort to correlate euphoric subjective responses with more objective quantities that can be measured through the imaging, as described below.

The reward system is a collection of brain structures that regulates and controls behavior by inducing pleasurable effects. The core structures of the brain reward pathways are located in the limbic system, an anatomical and functional concept that has changed over time and that has connections to all parts of the central nervous system [Michael S. Mega, Jeffrey L. Cummings, Stephen Salloway, Paul Malloy. The limbic system: an anatomic, phylogenetic, and clinical perspective. Journal of Neuropsychiatry and Clinical Neurosciences 9 (1997):315-330; Tim Dalgleish. The emotional brain. Nat Rev Neurosci. 5(7, 2004):583-589]. In its most basic conception, the limbic system can be defined by its input from dopaminergic neurons originating in the ventral tegmental area of the brain.

The neural circuitry most closely linked to positive reinforcement is the mesocorticolimbic dopaminergic system [Fibiger H C, Phillips A G. Reward, motivation, cognition: psychobiology of mesotelencephalic dopamine systems. In: Mountcastle V B, Bloom F E, Geyer S R, eds. Handbook of physiology: the nervous system IV. Bethesda, Md.: American Physiological Society, 1986:647-675]. This system is composed of several brain stem and forebrain nuclei that include the ventral tegmental area (VTA), nucleus accumbens within the striatum, prefrontal cortex, amygdala, hippocampus and the septum. The ventral tegmental area consists of dopaminergic neurons that respond especially to glutamate. These cells respond when stimuli indicative of a reward are present. Neurons of the VTA often project to sites containing a dopamine transporter, which is a membrane-spanning protein that pumps the neurotransmitter dopamine out of the synapse and back into cytosol, from which other transporters sequester dopamine into vesicles for later storage and release. The nucleus accumbens consists mainly of GABA neurons and appears to be a region in which behavioral responses are elicited. The prefrontal cortex appears to be the region in which the significance of stimuli are determined. The basolateral amygdala projects into the nucleus accumbens and is thought to be important for motivation.

Activation of the mesocorticolimbic dopaminergic system may be necessary for the generation of euphoria, but activation of other pathways of the brain may also be required, or the activation of other pathways may greatly modulate euphoric effects. Some investigators believe that activation of the dopaminergic system induces a sensation of "wanting", while modulation of associated neural pathways generate the sensation of hedonic "liking". Such modulation generally involves the production and reception of endogenous substances, as now described. Several brain structures and pathways, notably in the hypothalmus and pituitary gland, produce endogenous opioid compounds such as enkephalins, endorphins, and dynorphins. These opiate pathways can directly stimulate VTA cells and thus cause release of dopamine in the nucleus accumbens. Opiate pathways can also cause the release of dopamine in the nucleus accumbens via direct input to this nucleus. The mechanisms include involvement of opioid receptors, which are presynaptic and inhibit the release of the inhibitory neurotransmitter GABA, thereby decreasing the inhibition of dopamine pathways and causing more dopamine to be released [Wise R A. Opiate reward: sites and substrates. Neurosci Biobehav Rev. 13(2-3, 1989): 129-33].

Furthermore, so-called "hedonic hotspots," where opioid or other signals cause amplification of reward signals via pathways connected to the mesolimbic dopaminergic system, are located in the nucleus accumbens shell, ventral pallidum, and possibly other forebrain and limbic cortical regions and also deep brainstem regions including the parabrachial nucleus in the pons [Kent C. Berridge & Morten L. Kringelbach. Affective neuroscience of pleasure: reward in humans and animals. Psychopharmacology (2008) 199:457-480].

Some such locations of the brain may also be activated by endocannabinoids rather than opioids [Pal PACHER, Sandor Batkai, and George Kunos. The Endocannabinoid System as an Emerging Target of Pharmacotherapy. Pharmacological Reviews September 2006 vol. 58 no. 3 389-462; Roger A. Nicoll and Bradley N. Alger. The Brain's Own Marijuana. Sci Am. 291(6, 2004):68-75]. Thus, endogeneous or exogenous opioids or cannabinoids may promote dopaminergic neurotransmission by inhibiting GABAergic transmission in the VTA and other sites. Stimulation of mu opioid receptors, GABA-A receptors, or CB1 cannabinoid receptors on VTA GABAergic neurons reduces GABA transmission, which increases the firing rate of dopaminergic neurons through disinhibition.

Most chemicals that cause euphoria are thought to do so directly or indirectly by stimulating the brain's reward system, by flooding the circuit with dopamine. Depressants such as alcohol, barbiturates, and benzodiazepines work by increasing the affinity of the GABA receptor for GABA, e.g., from the nucleus accumbens. Narcotics such as morphine and heroin work by mimicking endorphins or by disabling the neurons that normally inhibit the release of dopamine in the reward system. Stimulants such as amphetamines, nicotine, and cocaine increase dopamine signaling in the reward system either by directly stimulating its release or by blocking its absorption [George F. Koob, Pietro Paolo Sanna and Floyd E. Bloom. Neuroscience of Addiction. Neuron, Vol. 21 (2008), 467-476].

Neurochemical imaging investigations involving D2 dopamine receptors and dopamine active transporters confirm that enhanced dopaminergic activity is associated with euphoric or positive subjective responses that are induced by drugs such as cocaine, amphetamines, ecstasy, alcohol, cannabis, opiates and nicotine. The magnitude of euphorigenic effects was found to be dependent on the dopaminergic tone at baseline. Furthermore, functional imaging studies showed ventral tegmentum, basal ganglia, insula, anterior cingulate and orbito-frontal cortex as putative neuroanatomical substrates involved in the mediation of euphoric subjective responses [Voruganti L P, Awad A G. Brain imaging research on subjective responses to psychotropic drugs. Acta Psychiatr Scand 2005: 111 (Suppl. 427): 22-28].

Deep brain stimulation of the subthalamic nucleus has induced hypomania in Parkinson's disease patients [COENEN V A, Honey C R, Hurwitz T, Rahman A A, McMaster J, Bürgel U, Mädler B. Medial forebrain bundle stimulation as a pathophysiological mechanism for hypomania in subthalamic nucleus deep brain stimulation for Parkinson's disease. Neurosurgery. 2009 June; 64(6):1106-14]. Hypomania has also been induced by transcranial direct current stimulation and vagus nerve stimulation, but the mechanism of its induction is not as clear as the hypomania induced by deep brain stimulation [Abraham Patrick Arul-Anandam, Colleen Loo, and Philip Mitchell. Induction of Hypomanic Episode With Transcranial Direct Current Stimulation. Journal of ECT 26(1, 2010): 68-69; Klein J P, Jean-Baptiste M, Thompson J L, Bowers M B Jr. A case report of hypomania following vagus nerve stimulation for refractory epilepsy Clin Psychiatry. 2003 April; 64(4):485].

The mesocorticolimbic dopaminergic reward system also connects to motor and cognitive portions of the brain that are associated with smiling, laughing, and humorous, pleasant, or euphoric thoughts. Thus, deep brain stimulation of the right and left anterior limbs of the internal capsule and region of the nucleus accumbens elicits spontaneous euphoric half-smiles on the side of the mouth contralateral to the stimulating electrode, generating also a euphoric affect in the patient [Michael S. Okun, Dawn Bowers, Utaka Springer, Nathan A. Shapira, Donald Malone, Ali R. Rezai, Bart Nuttin, Kenneth M. Heilman, Robert J. Morecraft, Steven A. Rasmussen, Benjamin D. Greenberg, Kelly D. Foote, and Wayne K. Goodman. What's in a "Smile?" Intra-operative Observations of Contralateral Smiles Induced by Deep Brain Stimulation. Neurocase, 10(4): 271-279, 2004]. When the subthalamic nucleus is stimulated by deep brain stimulation in Parkinson's disease patients, current diffusion into the VTA and related areas induces mirthful laughter [Paul Krack, Rajeev Kumar, Claire Ardouin, Patricia Limousin Dowsey, John M. McVicker, Alim-Louis Benabid, M D, and Pierre Pollak. Mirthful Laughter Induced by Subthalamic Nucleus Stimulation. Movement Disorders 16 (5, 2001): 867-875]. Instead of current diffusion, the stimulation may also have also stimulated tributaries of the subthalmic nucleus to the medial forebrain bundle, which in turn connects multiple structures within the mesocorticolimbic dopaminergic reward system.

The above-mentioned reports follow a long history of experiments in which electrodes are implanted into the brain of a human subject, who is allowed to self-stimulate any one of many electrodes at many locations. The experiments of Robert Heath are the best known—he found that electrodes implanted in the septum, which according to his definition included the nucleus accumbens, produced euphoric sensations when stimulated [Alan E. Fuchs. The Production of Pleasure by Stimulation of the Brain: An Alleged Conflict Between Science and Philosophy. Philosophy and Phenomenological Research, 36 (4, 1976): 494-505]. Similar euphoria-producing experiments were conducted by Jose Delgado [John Horgan. The forgotten era of brain chips. Scientific American 293(4, 2005):66-73].

Motor and cognitive programs of the brain are distributed throughout the brain, so it is also possible to elicit affective responses from multiple parts of such pathways, which involve for example the facial muscles in smiling and laughter. Laughter can be induced by electrically stimulating the frontal cortex in the anterior part of the supplementary motor area, an area that is closely related to speech [Itzhak Fried, Charles L. Wilson, Katherine A. MacDonald, Eric J. Behnke. Electric current stimulates laughter. Nature 391 (1998): 650]. As described above in connection with deep brain stimulation, such smiling and laughing behavior can originate within the mesocorticolimbic dopaminergic reward system. Conversely, it is thought that reciprocal effects may to some extent stimulate the reward system. For example, imagining a humorous situation or smiling voluntarily might beget limbic spontaneous smiling, particularly a so-called Duchenne smile [Andreas Hennenlotter, Christian Dresel, Florian Castrop, Andres O. Ceballos-Baumann, Afra M. Wohlschlager and Bernhard Haslinger. The Link between Facial Feedback and Neural Activity within Central Circuitries of Emotion—New Insights from Botulinum Toxin—Induced Denervation of Frown Muscles. Cerebral Cortex 19 (2009):537-542; Ekman P, Davidson R J, Friesen W V. The Duchenne smile: Emotional expression and brain physiology II. Journal of Personality and Social Psychology. 1990; 58:342-353].

FIG. 1 is a schematic diagram of a nerve stimulating/modulating device 300 for delivering impulses of energy to nerves for the treatment of medical conditions. As shown, device 300 may include an impulse generator 310; a power source 320 coupled to the impulse generator 310; a control unit 330 in communication with the impulse generator 310 and coupled to the power source 320; and a magnetic stimulator coil 340 coupled via wires to impulse generator coil 310. The stimulator coil 340 is toroidal in shape, due to its winding around a toroid of core material.

Although the magnetic stimulator coil 340 is shown in FIG. 1 to be a single coil, in practice the coil may also comprise two or more distinct coils, each of which is connected in series or in parallel to the impulse generator 310. Thus, the coil 340 shown in FIG. 1 represents all the magnetic stimulator coils of the device collectively. In the preferred embodiment that is disclosed below, coil 340 actually contains two coils that may be connected either in series or in parallel to the impulse generator 310.

The item labeled in FIG. 1 as 350 is a volume, surrounding the coil 340, that is filled with electrically conducting medium. As shown, the medium not only encloses the magnetic stimulator coil, but is also deformable such that it is form-fitting when applied to the surface of the body. Thus, the sinuousness or curvature shown at the outer surface of the electrically conducting medium 350 correspond also to sinuousness or curvature on the surface of the body, against which the conducting medium 350 is applied, so as to make the medium and body surface contiguous. As described below in connection with a preferred embodiment, the volume 350 is electrically connected to the patient at a target skin surface in order to significantly reduce the current passed through the coil 340 that is needed to accomplish stimulation of the patient's nerve or tissue. As also described below in connection with a preferred embodiment, conducting medium in which the coil 340 is embedded need not completely surround the toroid.

The control unit 330 controls the impulse generator 310 to generate a signal for each of the device's magnetic stimulation coils. The signals are selected to be suitable for amelioration of a particular medical condition, when the signals are applied non-invasively to a target nerve or tissue via the magnetic stimulator coil 340. It is noted that nerve stimulating/modulating device 300 may be referred to by its function as a pulse generator. Patent application publications US2005/0075701 and US2005/0075702, both to SHAFER, both of which are incorporated herein by reference, relating to stimulation of neurons of the sympathetic nervous system to attenuate an immune response, contain descriptions of pulse generators that may be applicable to the present invention, when adapted for use with a magnetic stimulator coil. By way of example, a pulse generator 300 is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard and computer mouse as well as any externally supplied physiological signals, analog-to-digital converters for digitizing externally supplied analog signals, communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals.

Parameters for the nerve or tissue stimulation include power level, frequency and train duration (or pulse number). The stimulation characteristics of each pulse, such as depth of penetration, strength and accuracy, depend on the rise time, peak electrical energy transferred to the coil and the spatial distribution of the electric field. The rise time and peak coil energy are governed by the electrical characteristics of the magnetic stimulator and stimulating coil, whereas the spatial distribution of the induced electric field depends on the coil geometry and the anatomy of the region of induced current flow. In one embodiment of the invention, pulse parameters are set in such as way as to account for the detailed anatomy surrounding the nerve that is being stimulated [Bartosz SAWICKI, Robert Szmurło, Przemysław Płonecki, Jacek Starzyński, Stanisław Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. A single pulse may be monophasic (no current reversal within the coil), biphasic or polyphasic. For rapid rate stimulators, biphasic systems may be used wherein energy is recovered from each pulse in order to help energize the next. Embodiments of the invention include those that are fixed frequency, where each pulse in a train has the same inter-stimulus interval, and those that have modulated frequency, where the intervals between each pulse in a train can be varied.

Figure 2:
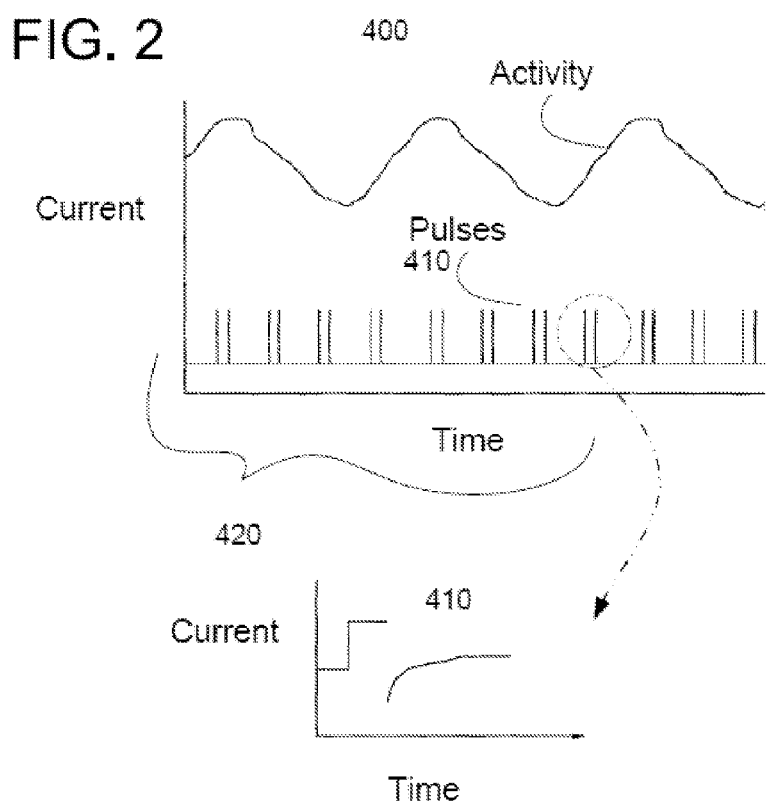
FIG. 2 illustrates an exemplary electrical voltage/current profile for a blocking and/or modulating impulses that are applied to a portion or portions of a nerve, in accordance with an embodiment of the present invention.

FIG. 2 illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively induced within the patient by the magnetic stimulator. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the stimulator coils(s) 340 that deliver the stimulating, blocking and/or modulating impulse 410 to the nerve. Nerve stimulating/modulating device 300 may be externally powered and/or recharged may have its own power source 320.

The parameters of the modulation signal 400 are preferably programmable, such as the frequency, amplitude, duty cycle, pulse width, pulse shape, etc. An external communication device may modify the pulse generator programming to improve treatment.

In addition, or as an alternative to the devices to implement the modulation unit for producing the electrical voltage/current profile of the stimulating, blocking and/or modulating impulse to the magnetic stimulator coil, the device disclosed in patent publication No. US2005/0216062 (the entire disclosure of which is incorporated herein by reference) may be employed. U.S. Patent Publication No.: 2005/0216062 discloses a multifunctional electrical stimulation (ES) system adapted to yield output signals for effecting electromagnetic or other forms of electrical stimulation for a broad spectrum of different biological and biomedical applications, including magnetic stimulators, which produce a high intensity magnetic field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated.

The stimulating, blocking and/or modulating impulse signal 410 preferably has a frequency, an amplitude, a duty cycle, a pulse width, a pulse shape, etc. selected to influence the therapeutic result, namely, stimulating, blocking and/or modulating some or all of the transmission of the selected nerve. For example, the frequency may be about 1 Hz or greater, such as between about 15 Hz to 50 Hz, more preferably around 25 Hz. The modulation signal may have a pulse width selected to influence the therapeutic result, such as about 20 microseconds or greater, such as about 20 microseconds to about 1000 microseconds. For example, the electric field induced by the device within tissue in the vicinity of a nerve is 10 to 600 V/m, preferably around 300 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz.

The preferred embodiment of magnetic stimulator coil 340 comprises a toroidal winding around a core consisting of high-permeability material (e.g., Supermendur or NAM-GLASS1 (also known as Metglass), manufactured by Magnetic Metals), embedded in an electrically conducting medium. Toroidal coils with high permeability cores have been theoretically shown to greatly reduce the currents required for transcranial (TMS) and other forms of magnetic stimulation, but only if the toroids are embedded in a conducting medium and placed against tissue with no air interface. [Rafael CARBUNARU and Dominique M. Durand. Toroidal coil models for transcutaneous magnetic stimulation of nerves. IEEE Transactions on Biomedical Engineering 48 (No. 4, April 2001): 434-441; Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, page 117 (UMI Microform Number: 9940153, UMI Company, Ann Arbor Mich.)].

In order to explain some of the novelty of the presently disclosed invention as compared with the device described in the above-mentioned Carbunaru and Durand publication, as well as in the FAIERSTEIN dissertation upon which the publication was based, it is useful to first summarize the relevant physics of electric fields and currents that are induced by time-varying magnetic fields, as produced by current-carrying coils [Richard P. FEYNMAN, Robert B. Leighton, and Matthew Sands. The Feynman Lectures on Physics. Volume II. Addison-Wesley Publ. Co. (Reading Mass., 1964), page 15-15; K. P. ESSELLE and M. A. Stuchly, Neural stimulation with magnetic fields: Analysis of induced electric fields, IEEE Trans. Biomed. Eng., 39 (July 1992), pp. 693-700; R. BOWTELL and R. M. Bowley. Analytic Calculations of the E-Fields Induced by Time-Varying Magnetic Fields Generated by Cylindrical Gradient Coils. Magnetic Resonance in Medicine 44:782-790 (2000); Feng LIU, Huawei Zhao, and Stuart Crozier. On the Induced Electric Field Gradients in the Human Body for Magnetic Stimulation by Gradient Coils in MRI, IEEE Transactions on Biomedical Engineering 50: (No. 7, July 2003) pp. 804-815].

The magnetic field B may be represented as the curl of a vector potential A, where B and A are functions of position and time: $B=\bar{\nabla}\times A$.

The electric field E, which is also a function of position and time, consists of two parts, $E_1$ and $E_2$: $E=E_1+E_2$. For a current-carrying coil, $E_1$ is obtained from the vector potential A by:

$$E_1 = -\frac{\partial A}{\partial t} = -\int \frac{1}{4\pi} \frac{\partial(\mu I)}{\partial t} \frac{dl}{r}$$

where $\mu$ is the permeability, I is the current flowing in the coil, dl is an oriented differential element of the coil, r is the distance between dl and the point at which the electric field E is measured, and the integral is performed around all the differential elements dl of the coil.

$E_2$ is obtained from the gradient of a scalar potential $\Phi$: $E_2 = \bar{\nabla}\Phi$. The scalar potential arises because conductivity changes along the path of a current, particularly the abrupt change of conductivity at an air/conductor interface, causes electric charges to separate and accumulate on the surface of the interface, with the amplitude and sign of the charges changing as a function of surface position. Thus, no conduction current can flow across an air/conductor interface, so according to the interfacial boundary conditions, the component of any induced current normal to the interface must be zero. The existence of a scalar potential accounts for these effects.

The electrical current density J, which is also a function of position and time, consists of two parts: $J=J_1+J_2$, corresponding to the two parts of E: $J_1=\sigma E_1$ and $J_2=\sigma E_2$, where the conductivity $\sigma$ is generally a tensor and a function of position. If the current flows in material that is essentially unpolarizable (i.e., is presumed not to be a dielectric), any displacement current may be ignored, so the current would satisfy Ampere's law:

$$\nabla \times \frac{B}{\mu} = J.$$

Because the divergence of the curl is zero, $\bar{\nabla}\cdot J=0$. One may substitute $J_1$ and $J_2$ into that equation to obtain: $\bar{\nabla}\cdot(\sigma(E_1-\bar{\nabla}\Phi))=0$. The latter equation has been solved numerically for special cases to estimate the currents that are induced by a magnetic field that is inserted into the body [W. WANG, S. R. Eisenberg, A three-dimensional finite element method for computing magnetically induced currents in tissues. IEEE Transactions on Magnetics. 30 (6, November 1994): 5015-5023; Bartosz SAWICKI, Robert Szmurło, Przemysław Pl/onecki, Jacek Starzyński, Stanisław Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. If the conductivity of material in the device (or patient) is itself selected to be a function of the electric field, then the equation becomes non-linear, which could exhibit multiple solutions, frequency multiplication, and other such non-linear behavior.

If the displacement current cannot be ignored, the displacement appears as a term involving the time-derivative of the electric field in the more general expression:

$$\nabla \cdot \left( \frac{\partial(\epsilon E)}{\partial t} + \sigma(E_1 - \nabla\Phi) \right) = 0,$$

where $\in$ is the permittivity, which is a function of position and is generally a tensor. As a consequence of such a term, the waveform of the electric field at any point will generally be altered relative to the waveform of the current I(t) that is passed through the coils. Furthermore, if the permittivity of a material in the device is itself selected to be a function of the electric field, then the equation becomes non-linear, which could exhibit multiple solutions, frequency multiplication, and other such non-linear behavior.

The above-mentioned publication by CARBUNARU and Durand, as well as the FAIERSTEIN dissertation upon which the publication was based, are heretofore unique in that they describe a magnetic stimulation device that does not create a magnetic field within the tissues that the device is intended to stimulate. Their device instead confines the magnetic field to a toroid, which is the only coil geometry known to create a magnetic field that is completely limited to part of space. With such a device, the electric field alone penetrates the patient to stimulate nerves or tissue, which they calculate using device-specific equations for the fields $E_1$ and $E_2$ that were defined above. Unlike conventional magnetic stimulation devices, their device's electric field orientation is not limited to fields at the skin that are parallel to the skin surface, due to the presence of conducting material that extends from the skin to (and beyond) the stimulator's coil. The boundary conditions giving rise to $E_2$ were those of an infinite half-space. Thus, their toroidal coil was immersed in a homogeneous continuous conducting material that had an air/conductor interface along an infinite plane parallel to the toroid, located at a variable distance from the toroid, and the toroid and conducting material were in contact with a patient's skin.

In their investigations, Carbunaru and Durand varied $E_1$ by only changing the coil geometry (integral over dl) as follows. They investigated winding the coil around different core geometries (round, quarter circle, square) and changed the radius and thickness of the core. They also varied $E_2$ by varying the thickness of the conducting layer in which the toroid was immersed, thereby changing boundary conditions only in that manner. Although Carbunaru and Durand demonstrated that it is possible to electrically stimulate a patient transcutaneously with such a device, they made no attempt to develop the device in such a way as to generally shape the electric field that is to stimulate the nerve. In particular, the electric fields that may be produced by their device are limited to those that are radially symmetric at any given depth of stimulation into the patient (i.e, z and p are used to specify location of the field, not x, y, and z). This is a significant limitation, and it results in a deficiency that was noted in FIG. 6 of their publication: "at large depths of stimulation, the threshold current [in the device's coil] for long axons is larger than the saturation current of the coil. Stimulation of those axons is only possible at low threshold points such as bending sites or tissue conductivity inhomogeneities". Thus, for their device, varying the parameters that they considered, in order to increase the electric field or its gradient in the vicinity of a nerve, may come at the expense of limiting the field's physiological effectiveness, such that the spatial extent of the field of stimulation may be insufficient to modulate the target nerve's function. Yet, such long axons are precisely what we may wish to stimulate in therapeutic interventions, such as the ones disclosed herein. Accordingly, it is an objective of the present invention to shape an elongated electric field of effect that can be oriented parallel to such a long nerve. The term "shape an electric field" as used herein means to create an electric field or its gradient that is generally not radially symmetric at a given depth of stimulation in the patient, especially a field that is characterized as being elongated or finger-like, and especially also a field in which the magnitude of the field in some direction may exhibit more than one spatial maximum (i.e. may be bimodal or multimodal) such that the tissue between the maxima may contain an area across which induced current flow is restricted. Shaping of the electric field refers both to the circumscribing of regions within which there is a significant electric field and to configuring the directions of the electric field within those regions.

Thus, the present invention differs from the device disclosed by CARBUNARU and Durand by deliberately shaping an electric field that is used to transcutaneously stimulate the patient. Our invention does so by configuring elements that are present within the equations that were summarized above, comprising (but not limited to) the following exemplary configurations that may be used alone or in combination.

First, the contours of the coil differential elements dl that are integrated in the above equation for $E_1$ are shaped into a geometry other than a single planar toroid. For example, two separate toroidal coils are used so that $E_1$ becomes the sum of two integrals, or the shape of a single toroid is twisted to resemble a figure-of-8 rather than a planar toroid.

Second, the value of the current I in the above equation for $E_1$ is manipulated to shape the electric field. For example, if the device contains two toroidal coils, the current in one toroid may be the negative of the current in the other toroid. As another example, the magnitude of the current in a left toroidal coil may be varied relative to the magnitude of the current in a right toroidal coil, so that the location of their superimposed induced electric fields may be correspondingly moved (focused) in the left or right directions. As another example, the waveform of the current in a left toroidal coil may be different than the waveform of the current in a right toroidal coil, so that their superimposed induced electric fields may exhibit beat frequencies, as has been attempted with electrode-based stimulators [U.S. Pat. No. 5,512,057, entitled Interferential stimulator for applying localized stimulation, to REISS et al.], and acoustic stimulators [ent No. U.S. Pat. No. 5,903,516, entitled Acoustic force generator for detection, imaging and information transmission using the beat signal of multiple intersecting sonic beams, to GREENLEAF et al].

Third, the scalar potential $\Phi$ in the above equation for $E_2$ is manipulated to shape the electric field. For example, this is accomplished by changing the boundaries of conductor/air (or non-conductor) interfaces, thereby creating different boundary conditions. Whereas the toroid in the CARBUNARU and Durand publication was immersed in a homogeneous conducting half-space, this is not necessarily the case for our invention. Although our invention will generally have some continuously conducting path between the device's coil and the patient's skin, the conducting medium need not totally immerse the coil, and there may be insulating voids within the conducting medium. For example, if the device contains two toroids, conducting material may connect each of the toroids individually to the patient's skin, but there may be an insulating gap (from air or some other insulator) between the surfaces at which conducting material connected to the individual toroids contact the patient. Furthermore, the area of the conducting material that contacts the skin may be made variable, by using an aperture adjusting mechanism such as an iris diaphragm. As another example, if the coil is wound around core material that is laminated, with the core in contact with the device's electrically conducting material, then the lamination may be extended into the conducting material in such a way as to direct the induced electrical current between the laminations and towards the surface of the patient's skin. As another example, the conducting material may pass through apertures in an insulated mesh before contacting the patient's skin, creating thereby an array of electric field maxima.

Fourth, the conductivity $\sigma$ (in the equations $J_1=\sigma E_1$ and $J_2=\sigma E_2$) may be varied spatially within the device by using two or more different conducting materials that are in contact with one another, for given boundary conditions. The conductivity may also be varied by constructing some conducting material from a semiconductor, which allows for adjustment of the conductivity in space and in time by exposure of the semiconductor to agents to which they are sensitive, such as electric fields, light at particular wavelengths, temperature, or some other environmental variable over which the user of the device has control. For the special case in which the semiconductor's conductivity may be made to approach zero, that would approximate the imposition of an interfacial boundary condition as described in the previous paragraph. As another example, the conducting material of the device may be selected to have a three-dimensional conductivity structure that approximates that of the conducting tissue under the patient's skin, but oriented in the opposite and/or mirror image directions, in such a way that the conductivity is symmetrical on either side of the patient's skin. Such an arrangement will allow for essentially symmetrical electrical stimulation of the patient's tissue and the conducting material within the device.

Fifth, a dialectric material having a high permittivity $\in$, such as Mylar, neoprene, titanium dioxide, or strontium titanate, may be used in the device, for example, in order to permit capacitative electrical coupling to the patient's skin.

Sixth, the present invention is more general than the device described in the above-mentioned publication of CARBUNARU and Durand in that, although the magnetic field produced by the present invention does not effectively penetrate the patient's tissue, that feature need not be due to the use of a toroidal coil. The magnetic field will not effectively penetrate the patient's tissue if the field's de minimis existence within the patient would produce no significant physiological effect. For example, it would not produce a significant physiological effect if the magnitude of the magnetic field were of the same order of magnitude as the earth's magnetic field. The magnetic field of our disclosed device may be produced by a coil other than a toroid, wherein the magnetic field outside the coil falls rapidly as a function of distance from the coil. For example, the coil may be a solenoid that has an approximately centrally-confined magnetic field as the density of coil turns and the length of the solenoid increase. As another example, the coil may be a partial toroid, which would also have a magnetic field that approximates that of a complete toroid as the gap within the partial-toroid decreases to zero. As another example, even if one is attempting to construct a complete toroidal winding, the presence of lead wires and imperfections of the winding may cause the device in practice to deviate from the ideal toroid. Such non-toroidal windings may be used in the present invention if they are backed away and/or oriented relative to the patient's skin in such a way that the magnetic field that is produced by the device does not effectively penetrate the patient's tissue. Alternatively, magnetic shielding, such as mumetal, supermalloy, supermumetal, nilomag, sanbold, molybdenum per-malloy, Sendust, M-1040, Hipernom and HyMu-80, may be interposed between the patient and coil of the device in such a way that the magnetic field that is produced by the device does not effectively penetrate the patient's tissue.

In the dissertation cited above, Carbunaru—FAIERSTEIN made no attempt to use conducting material other than agar in a KCl solution, and he made no attempt to devise a device that could be conveniently and safely applied to a patient's skin, at an arbitrary angle without the conducting material spilling out of its container. It is therefore an objective of the present invention to disclose conducting material that can be used not only to adapt the conductivity σ and select boundary conditions, thereby shaping the electric fields and currents as described above, but also to create devices that can be applied practically to any surface of the body. The volume of the container containing electrically conducting medium is labeled in FIG. 1 as 350. Use of the container of conducting medium 350 allows one to generate (induce) electric fields in tissue (and electric field gradients and electric currents) that are equivalent to those generated using current magnetic stimulation devices, but with about 0.001 to 0.1 of the current conventionally applied to a magnetic stimulation coil. This allows for minimal heating and deeper tissue stimulation. However, application of the conducting medium to the surface of the patient is difficult to perform in practice because the tissue contours (head for TMS, arms, legs, neck, etc. for peripheral nerve stimulation) are not planar. To solve this problem, in the preferred embodiment of the present invention, the toroidal coil is embedded in a structure which is filled with a conducting medium having approximately the same conductivity as muscle tissue, as now described.

In one embodiment of the invention, the container contains holes so that the conducting material (e.g., a conducting gel) can make physical contact with the patient's skin through the holes. For example, the conducting medium 350 may comprise a chamber surrounding the coil, filled with a conductive gel that has the approximate viscosity and mechanical consistency of gel deodorant (e.g., Right Guard Clear Gel from Dial Corporation, 15501 N. Dial Boulevard, Scottsdale Ariz. 85260, one composition of which comprises aluminum chlorohydrate, sorbitol, propylene glycol, polydimethylsiloxanes Silicon oil, cyclomethicone, ethanol/SD Alcohol 40, dimethicone copolyol, aluminum zirconium tetrachlorohydrex gly, and water). The gel, which is less viscous than conventional electrode gel, is maintained in the chamber with a mesh of openings at the end where the device is to contact the patient's skin. The gel does not leak out, and it can be dispensed with a simple screw driven piston.

In another embodiment, the container itself is made of a conducting elastomer (e.g., dry carbon-filled silicone elastomer), and electrical contact with the patient is through the elastomer itself, possibly through an additional outside coating of conducting material. In some embodiments of the invention, the conducting medium may be a balloon filled with a conducting gel or conducting powders, or the balloon may be constructed extensively from deformable conducting elastomers. The balloon conforms to the skin surface, removing any air, thus allowing for high impedance matching and conduction of large electric fields in to the tissue. A device such as that disclosed in U.S. Pat. No. 7,591,776, entitled Magnetic stimulators and stimulating coils, to PHILLIPS et al. may conform the coil itself to the contours of the body, but in the preferred embodiment, such a curved coil is also enclosed by a container that is filled with a conducting medium that deforms to be contiguous with the skin.

Agar can also be used as part of the conducting medium, but it is not preferred, because agar degrades in time, is not ideal to use against skin, and presents difficulties with cleaning the patient and stimulator coil. Use of agar in a 4M KCl solution as a conducting medium was mentioned in the above-cited dissertation: Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, page 117 (UMI Microform Number: 9940153, UMI Company, Ann Arbor Mich.). However, that publication makes no mention or suggestion of placing the agar in a conducting elastomeric balloon, or other deformable container so as to allow the conducting medium to conform to the generally non-planar contours of a patient's skin having an arbitrary orientation. In fact, that publication describes the coil as being submerged in a container filled with an electrically conducting solution. If the coil and container were placed on a body surface that was oriented in the vertical direction, then the conducting solution would spill out, making it impossible to stimulate the body surface in that orientation. In contrast, the present invention is able to stimulate body surfaces having arbitrary orientation. Examples making use of the present device show the body surface as having many different orientations that are incompatible with the disclosure in the above-cited dissertation.

That dissertation also makes no mention of a dispensing method whereby the agar would be made contiguous with the patient's skin. A layer of electrolytic gel is said to have been applied between the skin and coil, but the configuration was not described clearly in the publication. In particular, no mention is made of the electrolytic gel being in contact with the agar.

Rather than using agar as the conducting medium, the coil can instead be embedded in a conducting solution such as 1-10% NaCl, contacting an electrically conducting interface to the human tissue. Such an interface is used as it allows current to flow from the coil into the tissue and supports the medium-surrounded toroid so that it can be completely sealed. Thus, the interface is material, interposed between the conducting medium and patient's skin, that allows the conducting medium (e.g., saline solution) to slowly leak through it, allowing current to flow to the skin. Several interfaces are disclosed as follows.

One interface comprises conducting material that is hydrophilic, such as Tecophlic from The Lubrizol Corporation, 29400 Lakeland Boulevard, Wickliffe, Ohio 44092. It absorbs from 10-100% of its weight in water, making it highly electrically conductive, while allowing only minimal bulk fluid flow.

Another material that may be used as an interface is a hydrogel, such as that used on standard EEG, EKG and TENS electrodes [Rylie A GREEN, Sungchul Baek, Laura A Poole-Warren and Penny J. Martens. Conducting polymer-hydrogels for medical electrode applications. Sci. Technol. Adv. Mater. 11 (2010) 014107 (13 pp)]. For example it may be the following hypoallergenic, bacteriostatic electrode gel: SIGNAGEL Electrode Gel from Parker Laboratories, Inc., 286 Eldridge Rd., Fairfield N.J. 07004.

A third type of interface may be made from a very thin material with a high dielectric constant, such as those used to make capacitors. For example, Mylar can be made in submicron thicknesses and has a dielectric constant of about 3. Thus, at stimulation frequencies of several kilohertz or greater, the Mylar will capacitively couple the signal through it because it will have an impedance comparable to that of the skin itself. Thus, it will isolate the toroid and the solution it is embedded in from the tissue, yet allow current to pass.

The preferred embodiment of the magnetic stimulator coil 340 in FIG. 1 reduces the volume of conducting material that must surround a toroidal coil, by using two toroids, side-by-side, and passing electrical current through the two toroidal coils in opposite directions. In this configuration, the induced current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain peripheral nerves.

This preferred embodiment of the invention is shown in FIG. 3. FIGS. 3A and 3B respectively provide top and bottom views of the outer surface of the toroidal magnetic stimulator 30. FIGS. 3C and 3C respectively provide top and bottom views of the toroidal magnetic stimulator 30, after sectioning along its long axis to reveal the inside of the stimulator.

FIGS. 3A-3D all show a mesh 31 with openings that permit a conducting gel to pass from the inside of the stimulator to the surface of the patient's skin at the location of nerve or tissue stimulation. Thus, the mesh with openings 31 is the part of the stimulator that is applied to the skin of the patient.

Figure 3A:
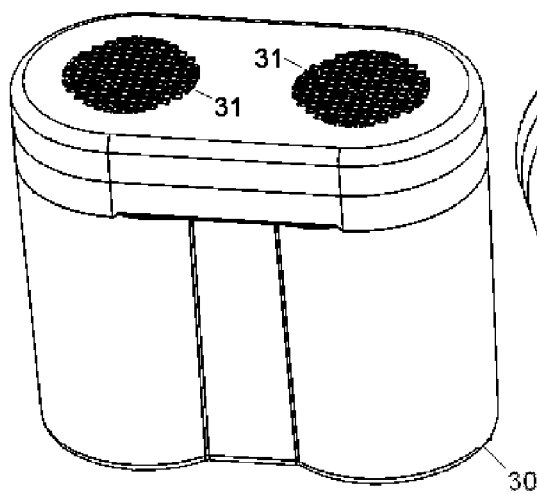
FIG. 3 illustrates a dual-toroid magnetic stimulator coil according to an embodiment of the present invention, which is shown to be situated within a housing that contains electrically conducting material.
Figure 3B:
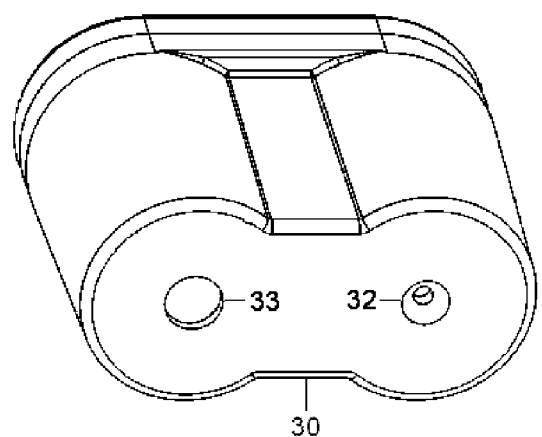
Figure 3C:
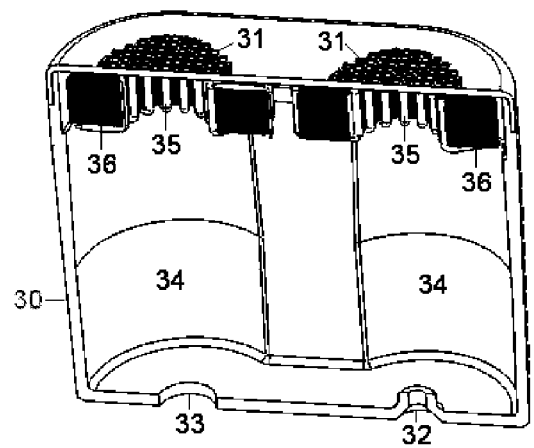
Figure 3D:
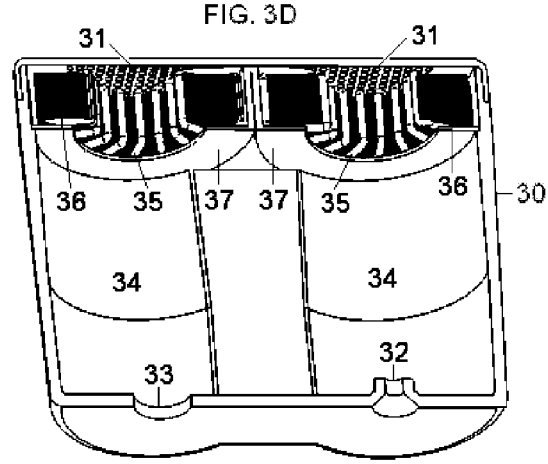

FIGS. 3B-3D show openings at the opposite end of the stimulator 30. One of the openings is an electronics port 32 through which wires pass from the stimulator coil(s) to the impulse generator (310 in FIG. 1). The second opening is a conducting gel port 33 through which conducting gel may be introduced into the stimulator 30 and through which a screw-driven piston arm may be introduced to dispense conducting gel through the mesh 31. The gel itself will be contained within cylindrical-shaped but interconnected conducting medium chambers 34 that are shown in FIGS. 3C and 3D. The depth of the conducting medium chambers 34, which is approximately the height of the long axis of the stimulator, affects the magnitude of the electric fields and currents that are induced by the device [Rafael CARBUNARU and Dominique M. Durand. Toroidal coil models for transcutaneous magnetic stimulation of nerves. IEEE Transactions on Biomedical Engineering. 48 (No. 4, April 2001): 434-441].

FIGS. 3C and 3D also show the coils of wire 35 that are wound around toroidal cores 36, consisting of high-permeability material (e.g., Supermendur or NAMGLASS1). Lead wires (not shown) for the coils 35 pass from the stimulator coil(s) to the impulse generator (310 in FIG. 1) via the electronics port 32. Different circuit configurations are contemplated. If separate lead wires for each of the coils 35 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As seen in FIGS. 3C and 3D, the coils 35 and cores 36 around which they are wound are mounted as close as practical to the corresponding mesh 31 with openings through which conducting gel passes to the surface of the patient's skin. As seen in FIG. 3D, each coil and the core around which it is wound is mounted in its own housing 37, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium.

Different diameter toroidal coils and windings may be preferred for different applications. For a generic application, the outer diameter of the core may be typically 1 to 5 cm, with an inner diameter typically 0.5 to 0.75 of the outer diameter. The coil's winding around the core may be typically 3 to 250 in number, depending on the core diameter and depending on the desired coil inductance.

The embodiment shown in FIG. 3 contains two toroids, in which the outer surface of the toroids are planar, the toroids lie side-by-side, and the corresponding outer surfaces for both toroids lie essentially in the same plane. Many different embodiments are also contemplated, each of which may be better suited to the stimulation of particular nerves or tissues. Examples of such alternate embodiments are illustrated in FIG. 4, showing the geometry of the toroidal core material around which coils of wire (not shown) would be wound. The darkened faces of the figures shown there indicate the faces that would be oriented towards the patient's skin. Instead of placing the toroids side-by-side as in FIG. 3, a pair of toroids may be placed concentrically as shown in FIG. 4A. Instead of using two toroids, any number could be used, as illustrated by FIG. 4B that shows four concentrically positioned toroids. Individual planar toroids need not all lie in the same plane, as shown in FIG. 4C. In fact, the toroids themselves need not have a planar structure, as illustrated in FIGS. 4D and 4E. Furthermore, the toroids need not have a round structure or a structure comprising arcs, as illustrated in FIG. 4F, which shows a pair of concentrically positioned square toroids. The examples shown here have toroids that are rectangular or square when sectioned perpendicular to their perimeters. In other embodiments, the sectioned toroid could have any other closed geometry, such as a circle or an ellipse or a geometry that changes from one part of the toroid to another.

Thus, the geometrical configuration of the disclosed device is general. For example, it may comprise a plurality of toroids. It may comprise two toroids wherein one toroid lies within the aperture of the second toroid. A surface having a minimum area that fills an aperture of a toroid need not lie within a plane. The projection of the volume of a toroidal core onto a plane need not produce a circular shape around any perimeter of any such projection. For a plurality of toroids, a plane having a greatest area of intersection through one toroid among the plurality may, but need not, be parallel to a plane having a greatest area of intersection through some second toroid among the plurality.

The design and methods of use of impulse generators, control units, and stimulator coils for magnetic stimulators are informed by the designs and methods of use of impulse generators, control units, and electrodes (with leads) for comparable completely electrical nerve stimulators, but design and methods of use of the magnetic stimulators must take into account many special considerations, making it generally not straightforward to transfer knowledge of completely electrical stimulation methods to magnetic stimulation methods. Such considerations include determining the anatomical location of the stimulation and determining the appropriate pulse configuration [OLNEY R K, So Y T, Goodin D S, Aminoff M J. A comparison of magnetic and electric stimulation of peripheral nerves. Muscle Nerve 1990:13:957-963; J. NILSSON, M. Panizza, B. J. Roth et al. Determining the site of stimulation during magnetic stimulation of the peripheral nerve, Electroencephalographs and clinical neurophysiology. vol 85, pp. 253-264, 1992; Nafia AL-MUTAWALY, Hubert de Bruin, and Gary Hasey. The Effects of Pulse Configuration on Magnetic Stimulation. Journal of Clinical Neurophysiology 20(5):361-370, 2003].

Figure 5:
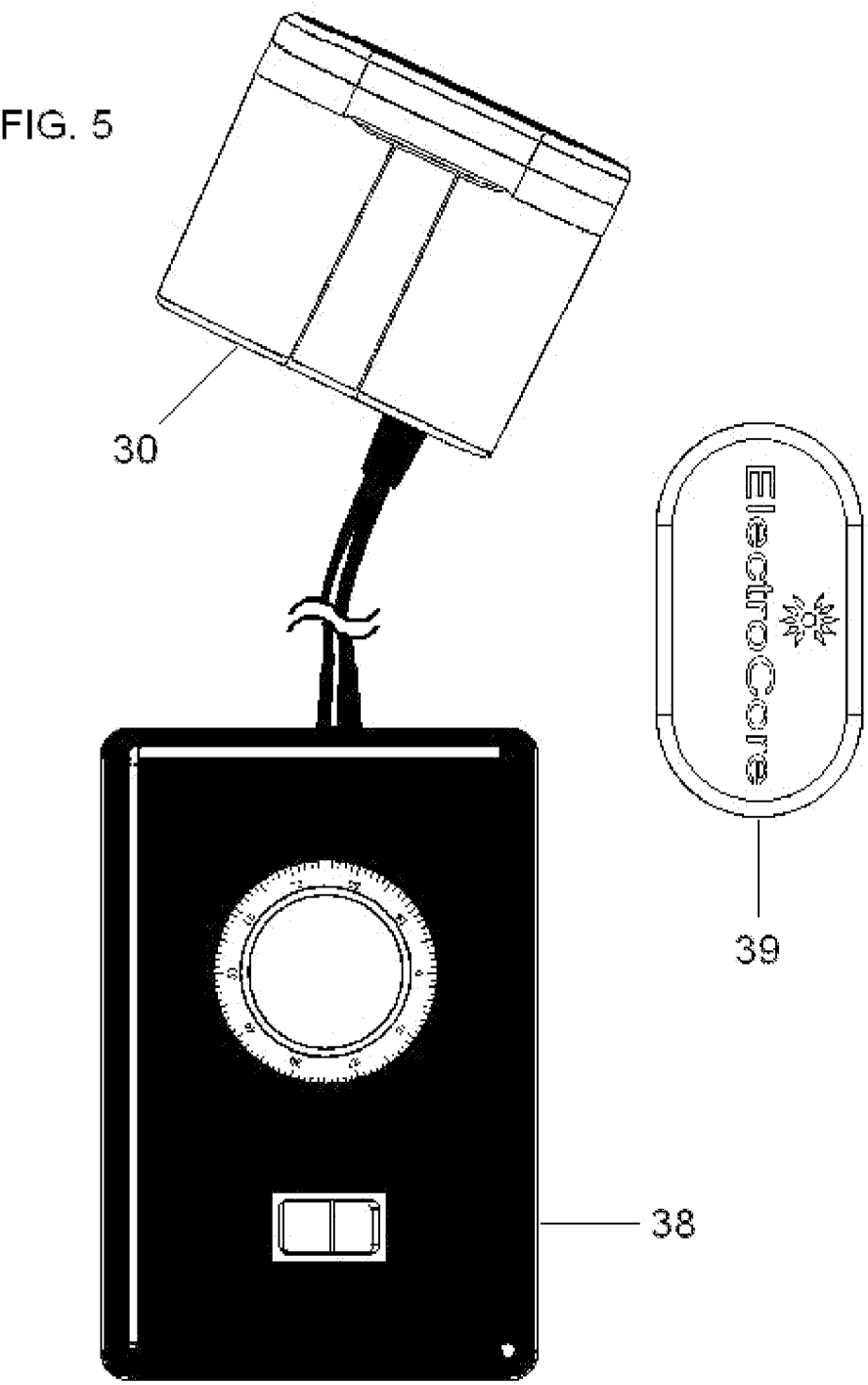
FIG. 5 illustrates the housing and cap of the dual-toroid magnetic stimulator coils of FIG. 3, attached via cable to a box containing the device's impulse generator, control unit, and power source.

In the preferred embodiment of the invention, electronic components of the stimulator (impulse generator, control unit, and power source) are compact, portable, and simple to operate. The preferred simplicity is illustrated in FIG. 5, which shows the stimulator coil housing 30 (illustrated in more detail as 30 in FIG. 3), which is connected by electrical cable to a circuit control box 38. As shown in FIG. 5, the circuit control box 38 will generally require only an on/off switch and a power controller, provided that the parameters of stimulation described in connection with FIG. 2 have already been programmed for the particular application of the device. For such a portable device, power is provided by batteries, e.g., the type of battery that is used to power a laptop computer. A covering cap 39 is also provided to fit snugly over the mesh (31 in FIG. 3) of the stimulator coil housing 30, in order to keep the housing's conducting medium from leaking or drying when the device is not in use.

In the preferred embodiment for a generic therapeutic application, the currents passing through the coils of the magnetic stimulator will saturate the core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses. The burst repeats at 1 Hz to 5000 Hz, preferably at 15-50 Hz. The pulses have duration of 20 to 1000 microseconds, preferably 200 microseconds and there may be 1 to 20 pulses per burst. Other waveforms described above in connection with FIG. 2 are also generated, depending on the nerve or tissue stimulation application.

Examples in the remaining disclosure will be directed to use of the disclosed toroidal magnetic stimulation device for treating a patient. These applications involve stimulating the patient in and around the patient's neck. However, it will be appreciated that the systems and methods of the present invention might be applied equally well to other nerves of the body, including but not limited to parasympathetic nerves, sympathetic nerves, and spinal or cranial nerves.

In some preferred embodiments of methods that make use of the disclosed toroidal-coil magnetic stimulation device, selected nerve fibers are stimulated. These include stimulation of the vagus nerve at a location in the patient's neck. At that location, the vagus nerve is situated within the carotid sheath, near the carotid artery and the interior jugular vein. The carotid sheath is located at the lateral boundary of the retopharyngeal space on each side of the neck and deep to the sternocleidomastoid muscle. The left vagus nerve is ordinarily selected for stimulation because stimulation of the right vagus nerve may produce undesired effects on the heart.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

Figure 6:
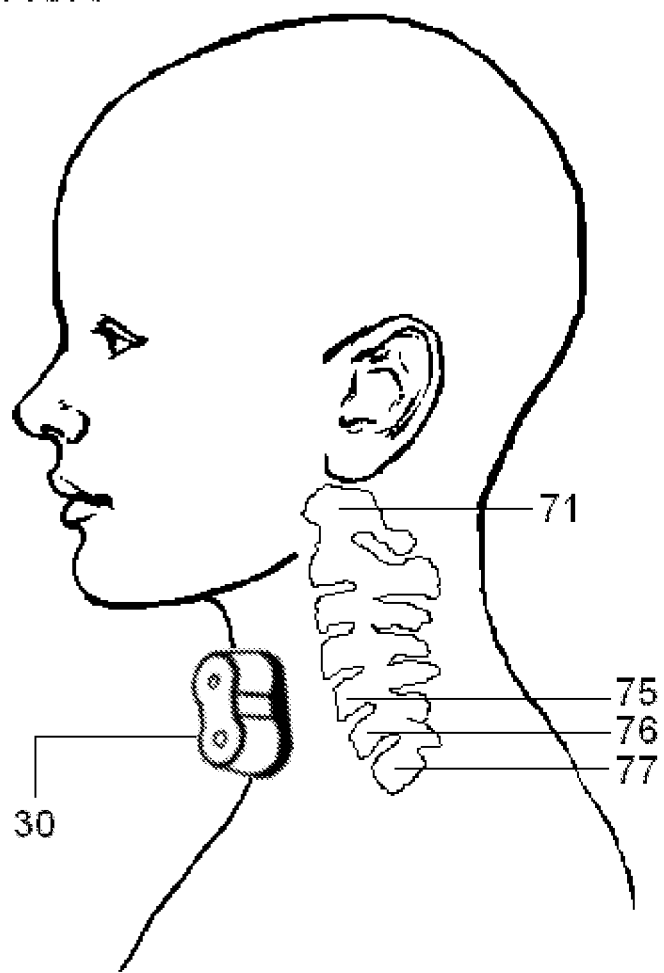
FIG. 6 illustrates the approximate position of the housing of the magnetic stimulator coil according one embodiment of the present invention, when the coil is used to stimulate the vagus nerve in the neck of a patient.

FIG. 6 illustrates use of the device shown in FIG. 3 and FIG. 5 to stimulate the vagus nerve at that location in the neck, in which the stimulator device 30 is applied to the target location on the patient's neck as described above. For reference, locations of the following vertebrae are also shown: first cervical vertebra 71, the fifth cervical vertebra 75, the sixth cervical vertebra 76, and the seventh cervical vertebra 77.

Figure 7:
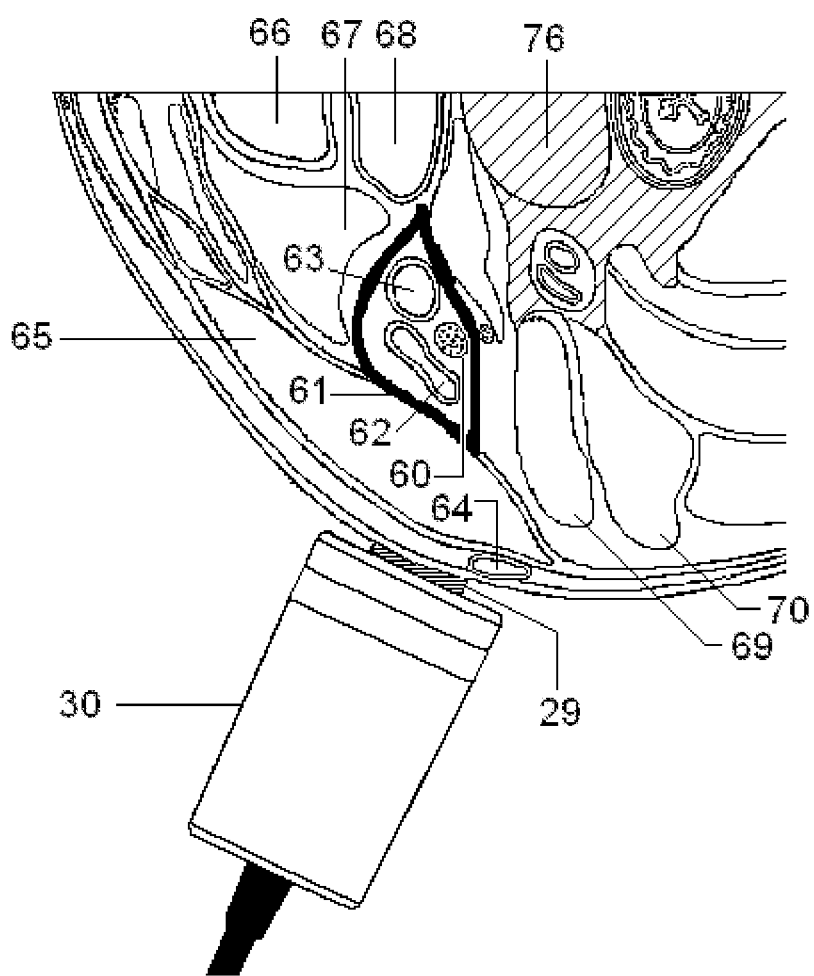
FIG. 7 illustrates the housing of the magnetic stimulator coil according one embodiment of the present invention, as the coil is positioned to stimulate the vagus nerve in a patient's neck via electrically conducting gel (or some other conducting material), which is applied to the surface of the neck in the vicinity of the identified anatomical structures.

FIG. 7 provides a more detailed view of use of the toroidal magnetic stimulator device, when positioned to stimulate the vagus nerve at the neck location that is indicated in FIG. 6. As shown, the toroidal magnetic stimulator 30 touches the neck indirectly, by making electrical contact through conducting gel 29 (or other conducting material) that is dispensed through mesh openings of the stimulator (identified as 31 in FIG. 3). The layer of conducting gel 29 in FIG. 7 is shown to connect the device to the patient's skin, but it is understood that the actual location of the gel layer(s) is generally determined by the location of mesh 31 shown in FIG. 3A. It is also understood that the device 30 is connected via wires or cables (not shown) to an impulse generator 310 as in FIG. 1. The vagus nerve 60 is identified in FIG. 7, along with the carotid sheath 61 that is identified there in bold peripheral outline. The carotid sheath encloses not only the vagus nerve, but also the internal jugular vein 62 and the common carotid artery 63. Features that may be identified near the surface of the neck include the external jugular vein 64 and the sternocleidomastoid muscle 65. Additional organs in the vicinity of the vagus nerve include the trachea 66, thyroid gland 67, esophagus 68, scalenus anterior muscle 69, and scalenus medius muscle 70. The sixth cervical vertebra 76 is also shown in FIG. 7, with bony structure indicated by hatching marks.

Magnetic stimulation has been used by several investigators to non-invasively stimulate the vagus nerve, in the neck and at other locations. In a series of articles beginning in 1992, Aziz and colleagues describe using non-invasive magnetic stimulation to electrically stimulate the vagus nerve in the neck. [Q. AZIZ et al. Magnetic Stimulation of Efferent Neural Pathways to the Human Oesophagus. Gut 33: S53-S70 (Poster Session F218) (1992); AZIZ, Q., J. C. Rothwell, J. Barlow, A. Hobson, S. Alani, J. Bancewicz, and D. G. Thompson. Esophageal myoelectric responses to magnetic stimulation of the human cortex and the extracranial vagus nerve. Am. J. Physiol. 267 (Gastrointest. Liver Physiol. 30): G827-G835, 1994; Shaheen HAM D Y, Qasim Aziz, John C. Rothwell, Anthony Hobson, Josephine Barlow, and David G. Thompson. Cranial nerve modulation of human cortical swallowing motor pathways. Am. J. Physiol. 272 (Gastrointest. Liver Physiol. 35): G802-G808, 1997; Shaheen HAMDY, John C. Rothwell, Qasim Aziz, Krishna D. Singh, and David G. Thompson. Long-term reorganization of human motor cortex driven by short-term sensory stimulation. Nature Neuroscience 1 (issue 1, May 1998):64-68.] SIMS and colleagues stimulated the vagus nerve at and near the mastoid tip. [H. Steven SIMS, Toshiyuki Yamashita, Karen Rhew, and Christy L. Ludlow. Assessing the clinical utility of the magnetic stimulator for measuring response latencies in the laryngeal muscles. Otolaryngol Head Neck Surg 1996; 114:761-7]. KHEDR and colleagues also used a magnetic stimulator to stimulate the vagus nerve at the tip of the mastoid bone [E. M. KHEDR and E-E. M. Aref Electrophysiological study of vocal-fold mobility disorders using a magnetic stimulator.

European Journal of Neurology 2002, 9: 259-267; KHEDR, E. M., Abo-Elfetoh, N., Ahmed, M. A., Kamel, N. F., Farook, M., El Karn, M. F. Dysphagia and hemispheric stroke: A transcranial magnetic study. Neurophysiologie Clinique/Clinical Neurophysiology (2008) 38, 235-242)]. SHAFIK stimulated the vagus nerve in the neck, placing the magnetic stimulator on the neck between the sternomastoid muscle and the trachea. [A. SHAFIK. Functional magnetic stimulation of the vagus nerve enhances colonic transit time in healthy volunteers. Tech Coloproctol (1999) 3:123-12]. Among these investigations, the one by SHAFIK stimulated the vagus nerve for the longest period of time. He stimulated at 175 joules per pulse, 40 Hz frequency, 10 seconds on, 10 seconds off for 20 minutes duration and followed by 60 minutes of rest, and this sequence was performed for 5 cycles in each subject.

The vagus is not the only nerve that may be stimulated non-invasively in the neck using magnetic stimulation. For example, the phrenic nerve has also been magnetically stimulated. [SIMILOWSKI, T., B. Fleury, S. Launois, H. P. Cathala, P. Bouche, and J. P. Derenne. Cervical magnetic stimulation: a new painless method for bilateral phrenic nerve stimulation in conscious humans. J. Appl. Physiol. 67(4): 1311-1318, 1989; Gerrard F. RAFFERTY, Anne Greenough, Terezia Manczur, Michael I. Polkey, M. Lou Harris, Nigel D. Heaton, Mohamed Rela, and John Moxham. Magnetic phrenic nerve stimulation to assess diaphragm function in children following liver transplantation. Pediatr Crit Care Med 2001, 2:122-126; W. D-C. MAN, J. Moxham, and M. I. Polkey. Magnetic stimulation for the measurement of respiratory and skeletal muscle function. Eur Respir J 2004; 24: 846-860]. If one intends to stimulate only the vagus nerve, careful positioning of the stimulator coil should be undertaken in order to avoid co-stimulation of the phrenic nerve, or the magnetic stimulation waveform may be designed to minimize the effect of any co-stimulation of the vagus and phrenic nerves [patent application JP2008/081479A, entitled Vagus nerve stimulation system, to YOSHIHOTO].

If it is desired to maintain a constant intensity of stimulation in the vicinity of the vagus nerve (or any other nerve or tissue that is being stimulated), methods may also be employed to modulate the power of the stimulator in order to compensate for patient motion or other mechanisms that would otherwise give rise to variability in the intensity of stimulation. In the case of stimulation of the vagus nerve, such variability may be attributable to the patient's breathing, which may involve contraction and associated change in geometry of the sternocleidomastoid muscle that is situated close to the vagus nerve (identified as 65 in FIG. 7). Methods for compensating for motion and other confounding factors were disclosed by the present applicant in co-pending application Ser. No. 12/859,568, published as US Pat. Pub. No. 2011/0046432, entitled Non-Invasive Treatment of Bronchial Constriction, to SIMON, which is hereby incorporated by reference.

The examples that follow exemplify therapies that involve stimulation of the vagus nerve in the neck using magnetic stimulation devices. However, it is understood that stimulation of the vagus nerve could also be performed at locations other than the neck [Polak T, Markulin F, Ehlis A C, Langer J B, Ringel T M, Fallgatter A J. Far field potentials from brain stem after transcutaneous vagus nerve stimulation: optimization of stimulation and recording parameters. J Neural Transm. 2009 October; 116(10):1237-42]. It is also understood that non-invasive methods other than magnetic stimulation may also be used to stimulate the vagus nerve, in order to achieve the intended therapeutic effects. In particular, the non-invasive methods and devices that Applicant disclosed in co-pending U.S. patent application Ser. No. 12/859,568, published as US Pat. Pub. No. 2011/0046432, entitled Non-invasive Treatment of Bronchial Constriction, to SIMON, may also be used. It is also understood that stimulation of nerves other than the vagus nerve might also achieve the intended therapeutic results, including those in the sympathetic nervous system.

In one preferred embodiment or the invention, a method of producing euphoria in a patient stimulates the vagus nerve as indicated in FIGS. 6 and 7, using the toroidal magnetic stimulation device that is disclosed herein. The position and angular orientation of the device are adjusted about that location until the patient perceives stimulation when current is passed through the stimulator coils. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6 or 7).

The stimulator signal may have a frequency and other parameters that are selected to induce a euphoric result in the patient. For example, current passing through a coil of the magnetic stimulation device may be about 0.5 to 20 amperes, typically 2 amperes, with voltages across each coil of 10 to 100 volts. The current is passed through the coils in bursts of pulses. The burst repeats at 1 Hz to 5000 Hz, preferably at 15-50 Hz, and typically 25 Hz. The pulses have duration of 20 to 1000 microseconds, preferably 200 microseconds, and there may be 1 to 20 pulses per burst. The stimulation may be performed for 1 to 200 minutes, typically for 1-2 minutes.

Parameters of the stimulation may be varied in order to obtain a euphoric response, as indicated by monitoring the response of the patient. That response is at least a Positive II and may progress to a Postive III, as follows:

(Positive II): The patient is definitely changed, is in a good mood, and feels good. He is relaxed, at ease, and enjoying himself. He frequently smiles. There is slight euphoria, but the behavior is within normal limits. He may want more stimulations.

(Positive III): The euphoria is definitely beyond normal limits. The patient may laugh out loud, enjoys himself, positively likes the stimulation and wants more.

The stimulation parameters for each patient are adjusted on an individualized basis. Ordinarily, the amplitude of the stimulation signal is set to the maximum that is comfortable for the patient, and then the other stimulation parameters are adjusted. Once the stimulation parameters that produce euphoria are found, an abrupt form of "rush" euphoria may occur within seconds. However, for some patients, a "rush" euphoria may not be possible without increasing the power of the stimulation to uncomfortable levels. In those individuals the euphoria increases gradually over the course of about ten minutes, during which time a Positive II euphoria may progress to a Positive III euphoria. In either case, the patient enters a euphoric "high" period, which may last about 3 to 6 hours, ending gradually after the stimulation is stopped.

During the euphoric period, the behavior of the patient is as defined by his or her Positive II or Positive III classification, as the case may be. Speech may be relaxed and slower than before the stimulation. No tendency to be easily distracted has been observed, as the patient may concentrate if requested. The patients exhibit an aura of well-being and exhibit sociability that is equal or greater than that exhibited before stimulation. The euphoric sensation is reported by some patients to resemble that induced by drugs, analogous to the sensation produced by a dissociative anesthetic such as nitrous oxide (laughing gas) used in dental offices. For some individuals, sleepiness is reported, and when the stimulation occurs just before bedtime, the onset of sleep occurs sooner than normal.

There has been no indication of hypomania being induced by the method. Patients do not exhibit irritability. There is no racing of thoughts. There is no urge to become active or productive. There is no feeling of grandiosity. There is no indication of the need for less sleep, and on the contrary the method may induce sleepiness in some individuals. There is no apparent deficit of attention. Although the patient may become more extroverted, there is no apparent loss of social inhibition as would be evidenced by objectionable language or conduct. There has been no indication of asymmetry in the ability to induce euphoria through the left versus right vagal nerves.

Figure 8:
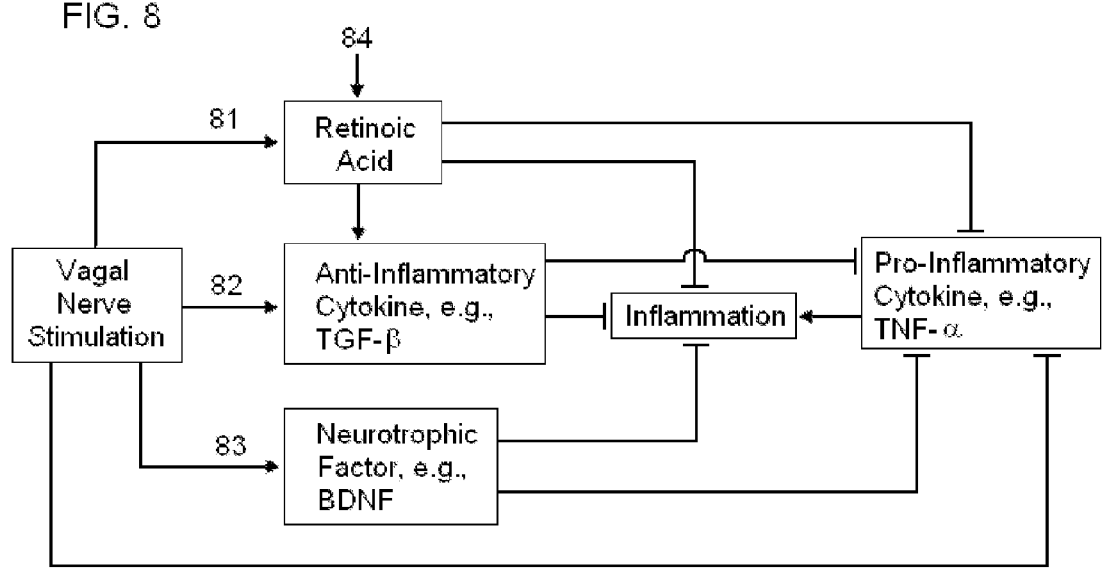
FIG. 8 illustrates mechanisms or pathways in the brain through which stimulation of the vagus nerve may produce euphoria in a patient.

FIG. 8 illustrates mechanisms or pathways through which stimulation of the vagus nerve may be used to produce euphoria in a patient. It is understood that the pathways shown there are a simplification of the actual mechanisms, that not all of the pathways may participate equally, that pathways not shown may also participate, and that future investigations may require that the pathways be modified.

Nevertheless, there exist known neural projections leading from the vagus nerve to the limbic regions of the brain that would explain the observed euphoric affect that is exhibited by patients who experience the stimulation procedures that are disclosed herein. Beginning in the lower right corner of FIG. 8, the vagus nerve is stimulated, and the resulting signal is sent towards the brain. Vagal afferents traverse the brainstem in the solitary tract, with some eighty percent of the terminating synapses being located in the nucleus of the tractus solitarius (NTS). The NTS projects to a wide variety of structures, as shown in FIG. 8, including the amygdala, the nucleus accumbens, and the hypothalamus [JEAN A. The nucleus tractus solitarius: neuroanatomic, neurochemical and functional aspects. Arch Int Physiol Biochim Biophys 1991; 99(5):A3-A52]. The NTS also projects to the parabrachial nucleus, which in turn projects to the hypothalamus, the thalamus, the amygdala, the anterior insular, and infralimbic cortex, lateral prefrontal cortex, and other cortical regions (only the thalamus projection is shown in FIG. 8). Other pathways from the NTS to the structures shown in FIG. 8 are multi-synaptic [M. CASTLE, E. Comoli and A. D. Loewy. Autonomic brainstem nuclei are linked to the hippocampus. Neuroscience 134 (2005) 657-669]. Through its direct and indirect projection to the amygdala and the nucleus accumbens, the NTS gains access to amygdala-hippocampus-entorhinal cortex pathways of the limbic system. The disclosed method of vagal nerve stimulation uses parameters (intensity, pulse-width, frequency, duty cycle, etc.) that preferentially activate the limbic system via the amygdala and nucleus accumbens or other routes [Jeong-Ho CHAE, Ziad Nahas, Mikhail Lomarev, Stewart Denslow, Jeffrey P. Lorberbaum, Daryl E. Bohning, Mark S. George. A review of functional neuroimaging studies of vagus nerve stimulation (VNS). Journal of Psychiatric Research 37 (2003) 443-455; G. C. Albert, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009) 1042 1060].

In its most basic conception, the limbic system can be defined by its input from dopaminergic neurons originating in the ventral tegmental area (VTA) of the brain. Those dopamine-producing neurons are shown in FIG. 8 as 81, projecting to the nucleus accumbens, with neurons branching nearby that project to the ventral palladium (VP) and prefrontal cortex (PFC). In addition, dopamine-producing neurons 81 project from the VTA to the amygdala and to the hippocampus. The "rush" that is felt by a euphoric individual is thought to occur when the VTA floods these dopaminergic neurons 81 with dopamine, thereby stimulating the nucleus accumbens, VP, PFC, amygdala, and hippocampus.

Feedback from the above-mentioned structures to the VTA determines the magnitude of the quasi-steady state "high" of dopamine levels during subsequent euphoria, as well as the steady state that obtained before the stimulation. The feedback loops involve neurons that use gamma-aminobutyric acid (GABA) as their neurotransmitter 82 as well as neurons that use glutamate as their neurotransmitter 83. The GABAminergic neurotransmission is generally inhibitory, while the glutamatergic neurotransmission is generally excitatory. As shown in FIG. 8, glutmatergic neurotransmission 83 occurs from the amygdala, PFC and hippocampus to the nucleus accumbens, as well as from the thalamus to the PFC. As also shown in FIG. 8, GABAminergic neurotransmission 82 occurs from the VTA and VP to the thalamus, from the nucleus accumbens to the VTA and VP, as well as within the VTA, which has the effect of inhibiting dopamine neurotransmission. The mechanism of inhibition is that a GABA-A receptor on the dopaminergic neuron binds to GABA released from a GABAminergic neuron, which inhibits dopaminergic neurotransmission. However, the GABAminergic neuron may contain mu-opioid and/or CB1 cannabinoid receptors on its surface. Mu opioid receptors are presynaptic, and inhibit neurotransmitter release. In particular, they inhibit the release of the inhibitory neurotransmitter GABA, and thereby disinhibit the dopamine pathways, causing more dopamine to be released.

Through such mechanisms, opioids and cannabinoids can indirectly modulate neurotransmission [Janice C. Froehlich. Opioid peptides. Alcohol health and research world. 132-136; Anupama Koneru, Sreemantula Satyanarayana and Shaik Rizwan. Endogenous Opioids: Their Physiological Role and Receptors. Global Journal of Pharmacology, 3 (3, 2009): 149-153; Julie LeMerrer, Jerome A. J. Becker, Katia Befort and Brigitte L. Kieffer. Reward Processing by the Opioid System in the Brain. Physiol Rev 89 (2009): 1379-1412]. Receptors for opioids are shown in FIG. 8 with a fork or goal-post symbol (µ), and the opioids that bind and activate them are shown with a solid square (■). Different types of opioid receptors that modulate neurotransmission are found throughout the brain, but significant ones for present purposes are shown in FIG. 8 in the VTA, nucleus accumbens, VP, parabrachial nucleus, and NTS. Similar receptors for cannabinoids exist throughout the brain (not shown). It is thought that without neuromodulation via the opioid and cannabinoid receptors, the dopmainergic limbic system may generate a feeling of "want", but with the additional receptor systems, a hedonic feeling of "like" (euphoria) may be generated [Julie LeMerrier, Jerome A. J. Becker, Katia Befort, and Brigitte L. Kieffer. Reward Processing by the Opioid System in the Brain. Physiol Rev 89 (2009): 1379-1412; Kent C. Berridge & Morten L. Kringelbach. Affective neuroscience of pleasure: reward in humans and animals. Psychopharmacology 199 (2008):457-480; Susana PECINA, Kyle S. Smith, and Kent C. Berridge. Hedonic Hot Spots in the Brain. Neuroscientist 12(6, 2006):500-511].

Endorphins are endogenous opioid peptides that function as neurotransmitters, and beta-endorphin is released into the brain from hypothalamic neurons. It is also released into the blood from the pituitary gland under the control of the hypothalamus, but because endorphins cannot pass easily through the blood-brain barrier, only the opioids under direct control of the hypothalamus are shown with the solid square (■) that is attached to the hypothalamus in FIG. 8. Thus, through the production of endogenous opioid peptides, the hypothalamus can modulate neurotransmission involving opioid receptors that were described above. The hypothalamus also connects bi-directionally to components of the limbic system, through the medial forebrain bundle. Such bidirectional connections are shown in FIG. 8 to the amygdala, nucleus accumbens, and VTA with arrows on both ends. [Pedro RADA, Jessica R. Barsonb Sarah F. Leibowitz, Bartley G. Hoebel. Opioids in the hypothalamus control dopamine and acetylcholine levels in the nucleus accumbens. Brain Research 1312 (2010) 1-9].

According to the foregoing description of FIG. 8, there are many pathways that may collectively bring about euphoria in the individual. From the NTS projections, direct inhibition of the nucleus accumbens and indirect inhibition via the amygdala may lead to a reduced GABAnergic signal from the nucleus accummbens to the VTA and VP. Inhibition of the thalamus via the parabrachial nucleus reduces stimulation of the prefrontal cortex, which in turn results in reduced stimulation of the nucleus accumbens. From the NTS input to the hypothalamus, stimulation may (1) produce endogenous opioids that can further inhibit GABAnergic inhibition through binding to the opioid receptors; and (2) directly stimulate the VTA and inhibit the amygdala and/or nucleus accumbens.

Such effects would bring about a significant dopaminergic neurotransmission disinhibition in the VTA, which responds by flooding the nucleus accumbens, amygdala, VP, PFC and hippocampus with dopamine along the dopaminergic projections 81, giving rise to a euphoric "rush". Continued stimulation of the vagus nerve prevents neurotransmitter equilibrium from being restored, during which time gene expression and other biochemical effects alter the physiology of the nerve cells. When stimulation is terminated, the duration of the subsequent euphoric high is a function of the time needed for neuronal changes, such as biochemical effects and gene expression that were altered during the stimulation, to be restored to their former equilibria.

The method disclosed above described the stimulation of a single vagus nerve, which may be the left vagus or the right vagus. However, in other embodiments of the invention, paired or multiple stimulation is also performed. For example, when the left and right vagus nerves are simultaneously stimulated, the same signal may be applied to both nerves, possibly with a delay of one with respect to the other (phase shift) in order to optimally entrain the two signals within the brain—mutually synchronizing/anti-synchronizing them in synergistic resonance, forming larger and more coherent neural ensembles than the neural ensembles associated with the individual signals. It is also understood that different sets of parameters may be used for stimulations of the left and right sides, in order to optimize the euphoric effect. For example, the interaction between neuronal signals may be non-linear, giving rise to non-linear effects such as frequency multiplication. In that embodiment of the invention, the frequency of stimulation of one vagus nerve may be a multiple of the frequency of stimulation of the other vagus nerve, and entrainment of the two signals may still occur.

In other embodiments of the invention, pairing of vagus nerve stimulation may be with a time-varying sensory stimulation. The sensory stimulation may be bright light, sound, tactile stimulation, or electrical stimulation of the tongue to simulate odor/taste, e.g., pulsating with the same frequency as the vagus nerve stimulation. The rationale for paired sensory stimulation is the same as the above-mentioned paired stimulation of left and right nerves, namely, that the pair of signals interacting with one another in the brain may result in the formation of larger and more coherent neural ensembles than the neural ensembles associated with the individual signals, thereby enhancing the experience of euphoria. For example, the hypothalamus shown in FIG. 8 is well known to be responsive to the presence of bright light, so exposing the patient to bright light that is fluctuating with the same stimulation frequency as the vagus nerve (or a multiple of that frequency) may be performed as an attempt to enhance the role of the hypothalamus in producing euphoria. Such paired stimulation does not rely upon neuronal plasticity and is in that sense different from other reports of paired stimulation [Navzer D. Engineer, Jonathan R. Riley, Jonathan D. Seale, Will A. Vrana, Jai A. Shetake, Sindhu P. Sudanagunta, Michael S. Borland and Michael P. Kilgard. Reversing pathological neural activity using targeted plasticity. Nature (2011): published online doi:10.1038/nature09656.].

In other embodiments of the invention, enhancement of the euphoria produced through stimulation of the vagus nerve may be obtained by first placing the patient in an environment and physiological state that is conducive to pleasure. This may involve relaxed deep breathing prior to the vagus nerve stimulation, meditation in which the patient is asked to image a loved one, showing a picture of a loved one, or asking the patient to voluntarily smile. These activities may also be conducted while the vagus nerve stimulation is in progress.

As now described, the disclosed methods and devices may be used for purposes of anesthesia or as a sleep aid for insomnia. They may also be useful therapeutically as a controlled substitute and withdrawal tool for individuals who otherwise would depend on unsafe substances and behaviors to achieve a euphoric state of mind, particularly individuals who abusively consume food, alcohol, tobacco or drugs, or who exhibit behavioral disorders such as compulsive gambling. The methods and devices provide a novel way to treat depression and/or premenstrual syndromes. They may also be useful to prevent, manage, or relieve mental or physical stress, thereby reducing the likelihood or severity of consequent health problems such as hypertension, strokes, heart attacks, diabetes, ulcers, and neck or low back pain. In general, one advantage of the disclosed methods is that they may produce euphoria more rapidly and conveniently than other agents that produce euphoria, without producing any known side-effects.

Example

Use for Anesthesia

As noted above, the euphoria that is induced by the disclosed methods resembles in some individuals a euphoria that is induced by drugs, analogous to the sensation produced by a dissociative anesthetic such as nitrous oxide (laughing gas) that is used in dental offices. Accordingly, one application of the methods is to use it for purposes of anesthesia. An advantage of doing so is that the device used to stimulate the vagus nerve is portable, and it requires only a source of electrical power to operate, such as a rechargeable laptop computer battery. Consequently, the device may be used in environments in which the delivery of anesthesia equipment and reagents would be a problem, such as on a battlefield or remote disaster scene, or in house-visit dentistry or minor surgery. It may also be appropriate for patients that are unusually sensitive to conventional anesthetics. Electrical stimulation for nerve blockage has been reported for use by anesthesiologists, but such methods and devices do not produce dissociative anesthesia and they do not result in euphoria. For example, patent U.S. Pat. No. 4,676,257 entitled Dental anesthesia apparatus to HALPERN describes transcutaneous electrical nerve stimulation to control pain but does not describe the induction of euphoria. Similarly, application US20070032841 entitled Nerve stimulation system with programmed pulse charge attenuation to URMEY describes a nerve stimulation system for regional anesthesia, but it too does not describe the induction of euphoria.

Example

Treatment of Insomnia

As noted above, the euphoria that is induced by the disclosed methods produces in some individuals sleepiness and the ability to fall asleep readily. Accordingly, one application of the methods is to use them as soporific agents, sedatives, or as a treatment for insomnia. An advantage of doing so over the use of sedative medications is that the medications such as benzodiazepines cause physical dependence and have side effects. Treatment of insomnia through electrical stimulation of the nervous system has been described, but such methods to no involve the induction of euphoria. For example, patent application US20100286734, entitled Treatment of Conditions Through Modulation of the Autonomic Nervous System to YUN et al. involves such an approach, but it does not involve the induction of euphoria.

Example

Treatment of Depression

Until the mid-1950s, a standard pharmacological treatment for clinical depression was to administer opioids. Opioids are recognized to be very effective in relieving the symptoms of depression, but their use was discontinued in the 1950s because they also cause addiction and physical dependence. More recently, only the opioid buprenorphineare is used on a limited basis to treat depression [BODKIN, J. Alexander, Zornberg, Gwen L., Lukas, Scott E., Cole, Jonathan O. Buprenorphine treatment of refractory depression. Journal of Clinical Psychopharmacology 15(1, 1995): 49-57]. Buprenorphine causes euphoria, but not the "rush" that is induced by many other opioids. Similarly, amphetamines were widely used to treat clinical depression until the 1970s and are considered to be effective in treating symptoms of fatigue, apathy, and resignation, although responses to amphetamines are more idiosyncratic than responses to opioids. Amphetamines too cause euphoria in patients, thereby relieving depression symptoms. However, use of amphetamines to treat depression was generally discontinued in the 1970s, because they too cause addiction and physical dependence. Today, they are used infrequently to treat depression, in selected populations of individuals who have other serious and sometimes terminal illnesses [Prakash S. MASAND and George E. Tesar. Use of stimulants in the medically ill. Psychiatric Clinics of North America 19(3, 1996): 515-547]. Ketamine is another drug that is sometimes used to treat depression. Ketamine is commonly used as an anesthetic, especially in veterinary medicine, and it has also been used to treat alcohol dependence, but it has side effects such as increased heart rate, nausea, and eventual cognitive impairment. At certain doses, ketamine produces euphoria and is therefore consumed by drug abusers. When used to treat depression, ketamine produces effects much more quickly than conventional antidepressant medication [Nancy A. Melville. Bolus Dose of Ketamine Offers Fast-Acting Alleviation of Acute Depression in ED Setting. Medscape Medical News (2010): Article 729622; Carlos A. Zarate, Jaskaran B. Singh, Paul J. Carlson, Nancy E. Brutsche, Rezvan Ameli, David A. Luckenbaugh, Dennis S. Charney, Husseini K. Manji. A Randomized Trial of an N-methyl-D-aspartate Antagonist in Treatment-Resistant Major Depression. Arch Gen Psychiatry. 2006; 63:856-864].

The method of inducing euphoria that is disclosed herein has no known tendency to cause addiction or physical dependency, so its use may be more suitable to treat depression than the use of the opioids or amphetamines. The method may also be more suitable than using ketamine when there is concern for ketamine's side effects. The induction of euphoria in patients with depression may also be more effective than the current standard pharmacological treatments, which include administration of selective serotonin reuptake inhibitors (SSRIs), tricyclic antidepressants (TCAs), monoamine oxidase inhibitor (MAOIs), serotonin-norepinephrine reuptake inhibitors (SNRIs), noradrenergic and specific serotonergic antidepressants (NaSSAs), norepinephrine (noradrenaline) reuptake inhibitors (NRIs), and norepinephrine-dopamine disinhibitors (NDDIs). Efficacy of the latter standard antidepressant medications has never been conclusively demonstrated to be greater than that of a placebo, according to two Cochrane Collaboration reviews, whereas the opioids and amphetamines are generally recognized to be effective, albeit addictive [MONCRIEFF J, Wessely S, Hardy R. Active placebos versus antidepressants for depression. Cochrane Database of Systematic Reviews 2004, Issue 1. Art. No.: CD003012]. Furthermore, the standard antidepressants ordinarily take several weeks before producing an effect, whereas the disclosed method produces effects within minutes or hours.

The therapeutic effects of standard antidepressant medications are believed to be caused by their effects on neurotransmitters and neurotransmission. In particular, they are intended to promote the re-establishment of more normal serotonin and norepinephrine levels, which are abnormal in depressed individuals [Kerry J. RESSLER and Charles B. Nemeroff. Role of serotonergic and noradrenergic systems in the pathophysiology of depression and anxiety disorders. Depression and Anxiety 12 (Supplement 1, 2000):2-19]. The induction of euphoria as disclosed herein is not based upon such normalization of serotonin and norepinephrine levels.

Vagal nerve stimulation (VNS) was first studied in the 1990s to treat depression that could not be treated with standard anti-depressant medications. As currently practiced, vagal nerve stimulation has limited effectiveness in treating depression. For example, the Technology Evaluation Center of Blue Cross/Blue Shield found that available data are insufficient to support the effectiveness of VNS therapy for depression [ANONYMOUS. Vagus Nerve Stimulation for Treatment-Resistant Depression. TEC Assessment Program 21 (7, 2006)]. Unlike the present invention that relieves symptoms of depressed individuals within minutes or hours, vagal nerve stimulation as it is currently practiced for the treatment of depression is not expected to produce any significant effects for many months [Steven C. Schachter. Vagus nerve stimulation: mood and cognitive effects. Epilepsy & Behavior 5 (2004) S56-S59; Ciaran D. Corcoran, Philip Thomas, Jack Phillips, and Veronica O'Keane. Vagus nerve stimulation in chronic treatment-resistant depression. Preliminary findings of an open-label study. British Journal of Psychiatry 189 (2006): 282-283]. The patient's manual that is provided by a manufacturer of VNS equipment indicates that only 15 percent of depressed patients respond within 3 months, and only 30 percent respond within a year. That manual notes that "The benefits of VNS Therapy are not always seen right away. In fact, depressive symptoms may improve slowly over the first year of treatment" ["Patient's Manual. For Vagus Nerve Stimulation with the VNS Therapy™ System. March 2004". Publication REF 26-0005-6000/1. Cyberonics, Inc., Houston, Tex. (Table 1 and pages 16-21)].

Because the effects of VNS using the method disclosed herein occur almost immediately, but effects using currently-practiced VNS may take a year to occur, the two VNS treatments must have different mechanisms that operate on different time scales. The mechanism by which vagal nerve stimulation as it is currently practiced for the treatment of depressed individual is not know in any detail, but it purportedly affects some of the same neural circuits that are modified by standard anti-depressant medication [Eric J. Nestler, Michel Barrot, Ralph J. DiLeone, Amelia J. Eisch, Stephen J. Gold, and Lisa M. Monteggia. Neurobiology of Depression. Neuron 34 (2002), 13-25; Joseph L Price and Wayne C Drevets. Neurocircuitry of Mood Disorders. Neuropsychopharmacology Reviews 35 (2010), 192-216]. Neural pathways through the locus coeruleus appear to be critical in VNS treatment for depression as it is currently practiced, particularly in epilepsy patients for which treatment for depression was developed. More specifically, norepinephrine (from the locus coeruleus) and serotonin (from the dorsal raphe and other raphe nuclei) are thought to underlie the mechanism of currently-practiced VNS, but not the mechanism shown in FIG. 8 [Thomas R. HENRY. Therapeutic mechanisms of vagus nerve stimulation. Neurology 59(6, 2002): S3-S14; Mark S. GEORGE, Ziad Nahas, Daryl E. Bohning, Qiwen Mu, F. Andrew Kozel, Jeffrey Borckhardt, Stewart Denslow. Mechanisms of action of vagus nerve stimulation (VNS). Clinical Neuroscience Research 4 (2004) 71-79; Sally P. WALSH and Mitchel A Kling. VNS and depression: current status and future directions. Expert Rev. Medical Devices 1(1, 2004):155-160; GROVES DA, Brown V J. Vagal nerve stimulation: a review of its applications and potential mechanisms that mediate its clinical effects. Neurosci Biobehav Rev (2005) 29:493-500; Charles B Nemeroff, Helen S Mayberg, Scott E Krahl, James McNamara, Alan Frazer, Thomas R Henry, Mark S George, Dennis S Charney and Stephen K Brannan. VNS Therapy in Treatment-Resistant Depression: Clinical Evidence and Putative Neurobiological Mechanisms. Neuropsychopharmacology (2006) 31, 1345-1355; Mark S George and Gary Aston-Jones. Noninvasive techniques for probing neurocircuitry and treating illness: vagus nerve stimulation (VNS), transcranial magnetic stimulation (TMS) and transcranial direct current stimulation (tDCS). Neuropsychopharmacology Reviews (2010) 35, 301-316]. Conversely, the present invention involves modulation of glutamate or glutamate receptors (Pathways 83 in FIG. 8), but currently-practiced VNS has not been associated with glutamate. In regards to the involvement of glutamate, the present invention resembles some non-standard antidepressant medications, including ketamine [Phil Skolnick, Beata Legutko, Xia Li and Frank P. Bymaster. Current perspectives on the development of non-biogenic amine-based antidepressants. Pharmacological Research 43(5, 2001):411-422; Husseini K. Manji, Jorge A. Quiroz, Jonathan Sporn, Jennifer L. Payne, Kirk Denicoff, Neil A. Gray, Carlos A. Zarate Jr., and Dennis S. Charney. Enhancing Neuronal Plasticity and Cellular Resilience to Develop Novel, Improved Therapeutics for Difficult-to-Treat Depression. Biol Psychiatry 53 (2003): 707-742]. However, it is understood that the present invention involves those pathways within a network, considering depression to be a network disorder rather than a perturbation in a single neurotransmitter or anatomical location in the brain [Aviva Abosch and G. Rees Cosgrove. Biological basis for the surgical treatment of depression. Neurosurg Focus 25 (1, 2008):E2 (pp. 1-12, DOI: 10.3171/FOC/2008/25/7/E2)]. It is also understood that unique mechanisms may also be involved in the pathophysiology and response to treatment in some depressed patients [Boulos-Paul Bejjani et al. Transient acute depression induced by high-frequency deep-brain stimulation. The New England Journal of Medicine 340(19, 1999) 1476-1480].

VNS as it is currently practiced may also induce a change in blood flow patterns in the brain [Astrid Zobel, Alexius Joe, Nikolaus Freymann, Hans Clusmann, Johannes Schramm, Michael Reinhardt, Hans-Jurgen Biersack, Wolfgang Maier, Karl Broich. Changes in regional cerebral blood flow by therapeutic vagus nerve stimulation in depression: An exploratory approach. Psychiatry Research: Neuroimaging 139 (2005) 165-179]. However, those are long-term blood flow changes, taking place over the course of four or more weeks. In contrast, exogenously administered opioids may also induce changes in blood flow within a matter of minutes, which may be associated with the feeling of "rush" euphoria [Thomas E. Schlaepfer, Eric C. Strain, Benjamin D. Greenberg, Kenzie L. Preston, Eric Lancaster, George E. Bigelow, Patrick E. Barta, and Godfrey D. Pearlson. Site of Opioid Action in the Human Brain: Mu and Kappa Agonists' Subjective and Cerebral Blood Flow Effects. Am J Psychiatry 155 (1998):470-473]. Although there is currently no evidence that activation of endogenous opioid systems by VNS is responsible for similar "rush" or "high" euphoric effects that are mediated via changes in brain blood flow, that remains a possible contributing mechanism for the present invention.

VNS may also increase levels of brain-derived neurotrophic factor (BDNF), the effects of which may elevate the mood of a depressed individual; but such effects are not part of the euphoric mechanism shown in FIG. 8 [Follesa P, Biggio F, Gorini G, Caria S, Talani G, Dazzi L, Puligheddu M, Marrosu F, Biggio G. Vagus nerve stimulation increases norepinephrine concentration and the gene expression of BDNF and bFGF in the rat brain. Brain Research 1179 (2007): 28-34]. However, repeated use of the disclosed VNS treatment might affect BDNF levels, for example, through glutamate mechanisms [Phil Skolnick, Beata Legutko, Xia Li and Frank P. Bymaster. Current perspectives on the development of non-biogenic amine-based antidepressants. Pharmacological Research 43(5, 2001):411-422; Joseph T. Coyle and Ronald S. Duman. Finding the Intracellular Signaling Pathways Affected by Mood Disorder Treatments. Neuron, Vol. 38 (2003): 157-160].

None of the purported mechanisms by which VNS as currently practiced works involve opioid receptors to any substantial extent, whereas the present invention may, as indicated in FIG. 8 [Susan E. Kennedy, Robert A. Koeppe, Elizabeth A. Young, Jon-Kar Zubieta. Dysregulation of Endogenous Opioid Emotion Regulation Circuitry in Major Depression in Women. Arch Gen Psychiatry. 2006; 63:1199-1208]. Applicants are unaware of any claim that vagal nerve stimulation, as it is currently practiced to treat epilepsy or depression, induces any form of euphoria other than unintended hypomania, and hypomania has not been found to be induced by the VNS method that is disclosed herein [Klein J P, Jean-Baptiste M, Thompson J L, Bowers M B Jr. A case report of hypomania following vagus nerve stimulation for refractory epilepsy. J Clin Psychiatry 64(4, 2003):485]. Furthermore, none of the literature discussing VNS as it is currently practiced describes or discusses substantial modulation of the neuronal circuits associated with the VTA, which are shown in FIG. 8. Within the patent literature, U.S. Pat. No. 7,747,326, entitled Method of treating mood disorders and/or anxiety disorders by brain stimulation to VALASCO et al. only indicates that euphoria is one of many listed emotions that might be influenced by nerve stimulation, but this is through an implanted electrode.

The euphoria-inducing method that is disclosed herein may be suitable for treating any of the classes of depression that are defined in the most recent version of the American Psychiatric Association Diagnostic and Statistical Manual of Mental Disorder. The method may be particularly suitable for treating individuals who have an acute-onset episode of depression, or in whom the symptoms of depression are severe, but less severe chronically depressed patients may be treated as well. Many scales have been devised for measuring severity of depression in an individual, including the Hamilton Rating Scale for Depression (HRSD), the Montgomery-Åsberg Depression Rating Scale (MADRS), the Beck Depression Inventory (BDI), the Zung Self-Rating Depression Scale, the Wechsler Depression Rating Scale, the Raskin Depression Rating Scale, the Inventory of Depressive Symptomatology (IDS), and the Quick Inventory of Depressive Symptomatology (QIDS), each of which may have variations [Hamilton, Max. A Rating Scale for Depression. Journal of Neurology, Neurosurgery, and Psychiatry. 23 (1960):56-62; Montgomery S A, Åsberg M. A new depression scale designed to be sensitive to change. Br J Psychiatry 134 (1979):382-389]. Psychiatrists disagree as to the significance that is to be attached to a particular numerical score, for example, whether a cutoff score of 7 or less is an acceptable definition for remission and whether a score of 20 or greater is consistent with major depressive disorder when using a HRSD 17-item score; and whether a cutoff score of 9 or less is an acceptable definition for remission using a MADRS score. However, it is understood that directional changes in a patient's score are a reflection of whether there is a corresponding change in the severity of depression. For purposes of specificity we adopt here the following definitions of response to treatment by the disclosed method. The definitions are also used in previous investigations of VNS responsiveness: Meaningful clinical benefit—25% to 49% improvement in depressive symptoms; Highly meaningful clinical benefit—50% to 74% improvement in depressive symptoms; Extraordinary clinical benefit—over 75% improvement in depressive symptoms; where improvement in symptoms is defined by a corresponding reduction in either HRSD or MADRS scores in an individual patient. Thus, the depressed individual (having been diagnosed by a psychiatrist or other medical professional and typically having a HRSD-17 score of 20 or greater) can be scored at pre-treatment baseline, then treated by the disclosed euphoria-producing method. The individual will then be scored periodically thereafter, for example after 20, 40, 80, 120, and 240 minutes, typically scoring with HRSD or MADRS measurements. At each such time point, the percent score reduction relative to baseline will be calculated, and this percent reduction determines whether the response to treatment is clinically meaningful, highly meaningful, or extraordinary.

Example

Treatment of Premenstrual Syndrome and Premenstrual Dysphoric Disorder

The disclosed euphoria-producing method is also useful for patients who suffer from symptoms that are related to depression, such as premenstrual syndrome (PMS) and its most intense form, premenstrual dysphoric disorder (PMDD). Most formal definitions of PMS require the presence of emotional symptoms such as unhappiness (dysphoria) as the chief complaint, with the exclusive presence of physical symptoms, such as abdominal cramps, not being considered to be PMS. Medical interventions for PMS and its most intense form, premenstrual dysphoric disorder, often include administration of the same selective serotonin reuptake inhibitors (SSRIs) that are used to treat depression [Nirav R. Shah, J. B. Jones, Jaclyn Aperi, Rachel Shemtov, Anita Karne, and Jeff Borenstein. Selective Serotonin Reuptake Inhibitors for Premenstrual Syndrome and Premenstrual Dysphoric Disorder: A Meta-Analysis. Obstet Gynecol. 111(5, 2008): 1175-1182]. Accordingly, the euphoria-producing method that is disclosed herein is presented as an alternative to the administration of anti-depressants as a treatment for PMS or PMDD. Assessing the severity of PMDD is often done with the Daily Record of Severity of Problems (DRSP) Short Form, which includes DSM-IV Criteria for PMDD [Jean Endicott. PMDD criteria. Diagnostic and Statistical Manual of Mental Disorders, American Psychiatric Association, 2000]. Symptomatic improvement following application of the disclosed euphoria-producing method may therefore be assessed based upon improvement according to the DSM-IV PMDD criteria.

Example

Stress Management

Mental or physical stress that is associated with a modern lifestyle (psychosocial stress) is a major independent risk factor for the likelihood of contracting certain diseases, as well as a factor influencing the severity of such diseases as hypertension, strokes, heart attacks, diabetes, ulcers, and neck or low back pain. Public health departments and medical professionals therefore not only encourage lifestyle change involving diet and exercise to manage the stress, but also encourage stressed individuals to participate in stress-reduction programs that teach relaxation, meditation, and biofeedback [Maxwell V. Rainforth, Robert H. Schneider, Sanford I. Nidich, Carolyn Gaylord-King, John W. Salerno, and James W. Anderson. Stress Reduction Programs in Patients with Elevated Blood Pressure: A Systematic Review and Meta-analysis. Curr Hypertens Rep. 9(6, 2007):520-528]. However, many individuals prefer to manage stress themselves, and it is a commonly held view that moderate alcohol consumption can reduce stress. Experimental investigations of the alcohol-stress relationship demonstrate that moderate alcohol consumption can in fact reduce stress in certain individuals. However, it may fail to do so in others depending on the age of the individual and whether the individual has a family history of alcoholism, has difficulty with self-control, performs well cognitively, and is easily distractible. The environment in which the individual ordinarily consumes alcohol also plays a role in determining whether that consumption relieves stress or not [Michael A. SAYETTE. Does drinking reduce stress? Alcohol Research and Health 23 (4, 1999):250-255].

Because the consumption of alcohol can induce euphoria in individuals, it is likely that the method for inducing euphoria that is disclosed herein can likewise be used to reduce stress. However, it is understood that such stress-reduction may not be possible in all individuals, for the same reasons that alcohol consumption does not reduce stress in all individuals. If the devices disclosed herein are made available to individuals for their own stress reduction program, then the devices may be adapted in such a way as to prevent over-use. For example, the devices may include circuitry that limits their use to a particular time of day, to a limited amount of stimulation per day, or to a limited stimulation intensity.

Example

Abused Drug Replacement Therapy

As noted above, use of many drugs of abuse produces euphoria, and for this reason those drugs can result in addiction and physical dependence. Withdrawal from many of them at the stage of drug tolerance is best done gradually and over a protracted period of time, otherwise cravings, withdrawal syndromes, seizures, rebound, and other problems may arise. One approach to the management of withdrawal is replacement therapy, in which a medically prescribed drug is substituted for the drug of abuse, such as replacing heroin with methadone. However, effective replacement therapies are not available for all drugs of abuse, and even when available, the therapy may fail as the patient finds other drugs for achieving euphoria, and total abstinence is difficult to achieve in practice [Rupert White. Dexamphetamine substitution in the treatment of amphetamine abuse: an initial investigation. Addiction 95(2, 2000), 229-238].

The method of producing euphoria that is disclosed herein may be useful as a substitution tool for managing substance abuse withdrawal, particularly if the substance does not already have an effective substitution therapy. If the drug of abuse is alcohol, the opioid receptor antagonist nalmefene is sometimes used for partial or total replacement therapy. Considering that the disclosed method and device produce euphoria that may be analogous to that produced by alcohol or opioids, the device may also be used for such partial or total replacement of alcohol or other drugs. In that application, the circuitry described above in connection with the management of stress may also be made programmable, such that the amount of stimulation that is allowed by the device can be tapered week-by-week as substitution of the euphoria-producing device for alcohol or drug consumption runs its course [Barbara J. MASON, Fernando R. Salvato, Lauren D. Williams, Eva C. Ritvo, Robert B. Cutler. A Double-blind, Placebo-Controlled Study of Oral Nalmefene for Alcohol Dependence. Arch Gen Psychiatry 56 (1999):719-724].

Example

Treatment of Behavioral Disorders

Behavioral disorders like compulsive gambling (ludomania) are impulse control disorders, rather than addictions, but they may be treated by methods that are similar to those for treating substance abuse. In particular, nalmefene is an opioid receptor antagonist used primarily in the management of alcohol dependence, but it is also used for the treatment of pathological gambling and compulsive shopping. As described above, the disclosed device and method for producing euphoria may be used by abusers of alcohol, in lieu of using nalmefene. So too, the device and method may be used by individuals with behavioral disorders, in lieu of treatment with a drug such as nalmefene. Thus, in cases involving the treatment of behavioral disorders, the disclosed devices and methods for producing euphoria are used to substitute for the problematic behavior that otherwise would produce euphoria [Jon E. GRANT, Marc N. Potenza, Eric Hollander, Renee Cunningham-Williams, Tommi Nurminen, Gerard Smits, Antero Kallio. Multicenter Investigation of the Opioid Antagonist Nalmefene in the Treatment of Pathological Gambling. Am J Psychiatry 163 (2006):303-312].

Example

Treatment of Eating Disorders

In binge eating disorders, the feeling of euphoria coincides with either the beginning or end of the eating binge. Individuals who suffer from bulimia nervosa reportedly experience euphoria as an antecedent to binge eating, similar to euphoria that may be produced by very prolonged fasting by normal individuals. A sense of euphoria may also terminate binge eating in eating disorders other than anorexia nervosa [Kjelsås E, Børsting I, Gudde C B. Antecendent and consequences of binge eating episodes in women with an eating disorder. Eat Weight Disord. 9 (1, 2004):7-15]. In yet another application of the invention, the euphoria-producing device may be provided to an individual suffering from such disorders. The individual suffering from bulimia nervosa may then use the device to induce euphoria and then begin eating, at a time earlier than the individual would have otherwise. Individuals suffering from eating disorders other than anorexia nervosa would use the device to induce euphoria during an eating binge, thus terminating the eating binge at a time earlier than the individual would have otherwise.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for modulating a state of mind of a patient, the method comprising:
   positioning a device in contact with an outer skin surface of a neck of the patient; and
   applying, via the device, energy transcutaneously and non-invasively through the outer skin surface of the neck of the patient to generate an electrical impulse at or near a vagus nerve within the patient, wherein the electrical impulse is sufficient to induce euphoria in the patient.

2. The method of claim 1, wherein the applying is carried out by generating a magnetic field exterior to the patient, wherein the magnetic field is sufficient to induce an electrical impulse at or near the vagus nerve within the patient.

3. The method of claim 1, wherein the electrical impulse is sufficient to stimulate nerve fibers that control or mediate an induction of the euphoria in the patient.

4. The method of claim 1 wherein the energy is applied to target a right branch of the vagus nerve.

5. The method of claim 1 wherein the energy is applied to target a left branch of the vagus nerve.

6. The method of claim 1, wherein a left branch and a right branch of the vagus nerve are stimulated simultaneously via the applying.

7. The method of claim 1, wherein the applying is carried out by:
   generating a time-varying magnetic field that is located essentially entirely outside of the patient;
   shaping an electric field that is induced by said magnetic field; and
   conducting an electric current that is induced by said magnetic field through the outer skin surface of the neck of the patient to modulate the vagus nerve.

8. The method of claim 1 wherein the vagus nerve is at least approximately 1-2 cm below an outer skin surface of the patient.

9. The method of claim 8, further comprising:
substantially constraining, via the device, an electric current from modulating one or more nerves in a region between the outer skin surface and the vagus nerve.

10. The method of claim 7 wherein the generating comprises generating the time-varying magnetic field within an enclosed coil.

11. The method of claim 10, wherein the enclosed coil is a first enclosed coil, wherein the shaping comprises generating a second time-varying magnetic field within a second enclosed coil positioned near or adjacent to the first enclosed coil.

12. The method of claim 10, wherein the shaping comprises positioning a conducting medium around a portion of the enclosed coil such that a direction of the electrical field is constrained within the conducting medium.

13. The method of claim 7, wherein the conducting is carried out by electrically coupling the induced electric field to a target region within the patient allowing current to flow through the outer skin surface of the neck of the patient.

14. The method of claim 1, wherein the electrical impulse is sufficient to cause dopaminergic neurons originating in a ventral tegmental area of a brain of the patient to stimulate neurons or tissue to which said dopaminergic neurons project.

15. The method of claim 14 wherein the stimulation by dopaminergic neurons is modulated by endogenous opioids and cannabinoids.

16. The method of claim 1 wherein the patient is in need of dissociative anesthesia.

17. The method of claim 1 wherein the patient is in need of sleep.

18. The method of claim 1 wherein the patient is depressed.

19. The method of claim 1 wherein the patient abuses drugs or alcohol and wherein the induced euphoria substitutes for consumption of said drugs or alcohol.

20. The method of claim 1 wherein the patient has an eating disorder and wherein the induced euphoria terminates an eating binge.

21. The method of claim 1 wherein the patient has bulimia nervosa and wherein the induced euphoria is used to cause the patient to eat.

22. The method of claim 1 wherein the induced euphoria is used to prevent or relieve psychosocial stress.

23. The method of claim 1 wherein the patient compulsively gambles or shops and wherein the induced euphoria substitutes for said compulsive gambling or shopping.

24. The method of claim 1, wherein the electrical impulse is based at least in part on an electric field with an amplitude of greater than about 10 V/m.

25. The method of claim 1, wherein the electrical impulse is based at least in part on an electric field with a gradient of greater than about 2 V/m/mm.

26. The method of claim 1, wherein the electrical impulse comprises bursts of pulses with a frequency from about 5 Hz to about 100 Hz.

27. The method of claim 1, wherein the electrical impulse comprises bursts from about 1 pulse to about 20 pulses with each of the pulses from about 50 microseconds to about 1000 microseconds in duration.

* * * * *